US008529928B2

(12) United States Patent
Wang et al.

(10) Patent No.: US 8,529,928 B2
(45) Date of Patent: Sep. 10, 2013

(54) BIOMIMETIC POLYMERS AND USES THEREOF

(75) Inventors: Yadong Wang, Allison Park, PA (US);
Blaine Zern, Atlanta, GA (US);
Christiane Gumera, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1168 days.

(21) Appl. No.: 12/307,073

(22) PCT Filed: Jul. 6, 2007

(86) PCT No.: PCT/US2007/072946
§ 371 (c)(1),
(2), (4) Date: Dec. 30, 2008

(87) PCT Pub. No.: WO2008/006064
PCT Pub. Date: Jan. 10, 2008

(65) Prior Publication Data
US 2009/0297607 A1    Dec. 3, 2009

Related U.S. Application Data

(60) Provisional application No. 60/819,219, filed on Jul. 7, 2006.

(51) Int. Cl.
| | |
|---|---|
| *A61K 31/765* | (2006.01) |
| *A61K 31/74* | (2006.01) |
| *A61K 47/34* | (2006.01) |
| *A61K 31/785* | (2006.01) |
| *A61K 31/095* | (2006.01) |
| *A61K 31/137* | (2006.01) |
| *A61K 31/191* | (2006.01) |
| *A61K 31/131* | (2006.01) |
| *A61K 31/198* | (2006.01) |
| *A61K 31/40* | (2006.01) |
| *A61K 31/41* | (2006.01) |
| *A61K 31/4164* | (2006.01) |

(52) U.S. Cl.
USPC ........... 424/422; 525/396; 525/540; 525/423; 525/449; 514/18.5; 514/653; 514/728; 514/738; 514/741; 514/739; 514/385; 514/183; 514/359; 514/657; 514/415; 514/711

(58) Field of Classification Search
USPC ................ 525/396, 540, 423, 449; 514/711, 514/415, 657, 359, 183, 385, 739, 741, 738, 514/728, 653
See application file for complete search history.

(56) References Cited

U.S. PATENT DOCUMENTS

| | | | |
|---|---|---|---|
| 5,360,610 A | 11/1994 | Tice et al. | |
| 7,049,285 B2 | 5/2006 | Park | |
| 2003/0036588 A1 | 2/2003 | Willett et al. | |
| 2003/0118692 A1* | 6/2003 | Wang et al. | ........................ 426/6 |

OTHER PUBLICATIONS

D'Arrigo et al. (Journal of Organic Chemistry, 62, Published 1997, pp. 6394-6396).*
Pillai (Textbook of Organic Chemistry, p. 174, Published by Universities Press (India) Private Ltd 2009).*
Alsberg, et al., "Engineering growing tissues", *Proc Natl Acad Sci USA*, 99(19):12025-30 (2002).
Anderson, et al., "Nanoliter-scale synthesis of arrayed biomaterials and application to human embryonic stem cells", *Nat Biotechnol*, 22(7):863-6 (2004). (abstract only).
Bendifallah, et al., "Evaluation of cell-penetrating peptides (CPPs) as vehicles for intracellular delivery of antisense peptide nucleic acid (PNA)", *Bioconjug Chem*, 17(3):750-8 (2006). (abstract only).
Camarata, et al. "Sustained release of nerve growth from biodegradable polymer microspheres", *Neurosurgery*, 30(3):313-9 (1992).
Cannizzaro, et al., "A novel biotinylated degradable polyer for cell-interactive applications", *Biotechnlol Bioeng*, 58(5):529-35 (1998). (abstract only).
Casper, et al., "Functionalizing electrospun fibers with biologically relevant macromolecules", *Biomacromolecules*, 6(4)1998-2007 (2005).
Check, et al., "Gene therapy put on hold as third child develops cancer", *Nature*, 433:561 (2005). (abstract only).
Cheng, et al., "A study of thermoresponsive poly(N-isopropylacrylamide)/polyarginine bioconjugate non-viral transgene vectors", *Biomaterials*, 27(28):4984-92 (2006). (abstract only).
Dalsin, et al., Mussel adhesive protein mimetic polymers for the prepration of nonfouling surfaces, *J Am Chem Soc*, 125(14):4253-8 (2003). (abstract only).
Deming, "Facile synthesis of block copolypeptides of defined architecture", *Nature*, 390(6658):386-9 (1997). (abstract only).
Evans, "Challenges to nerve regeneration", *Semin Surg Oncol*, 19(3):312-8 (2000). (abstract only).
Glover, et al., "Towards safe, non-viral therapeutic gene expression in humans", *Nat Rev Genet*, 6(4):299-310 (2005). (abstract only).
Hench and Polak, "Third-generation biomedical materials.", *Science*, 295(5557):1014-7 (2002).
Hubbell, "Bioactive biomaterials", *Curr Opin Biotechnol*, 10(2):123-9 (1999). (abstract only).
Hubbell, et al., "Endothelial cell-selective materials for tissue engineering in the vascular graft via a new receptor", *Biotechnology (NY)*, 9(6):568-72 (1991). (abstract only).
Hunter, "Molecular hurdles in polyfectin design and mechanistic background to polycation induces cytotoxicity", *Adv Drug Deliv Rev*, 58(14)1523-31 (2006). (abstract only).

(Continued)

*Primary Examiner* — Richard Schnizer
*Assistant Examiner* — Alma Pipic
(74) *Attorney, Agent, or Firm* — Pabst Patent Goup LLP

(57) ABSTRACT

Biodegradable polymers incorporating biomolecules and methods of their use are provided. Certain aspects provide biomolecules crosslinked with diglycidyl esters. The disclosed compositions have numerous applications including cellular regeneration, wound healing, and cellular differentiation.

17 Claims, 7 Drawing Sheets

(56) References Cited

OTHER PUBLICATIONS

Jon, et al., "Degradable poly(amino alcohol esters) as potential DNA vectors with low cytotoxicity", *Biomacromolecules*, 4(6):1759-62 (2003).

Kawakami, et al., "Neuronal attachment and outgrowth on a micropatterned fluorinated polyamide surface", *J Artif Organs*, 7(2):83-90 (2004). (abstract only).

Kim, et al., "Arginine-conjugated polypropylenimine dendrimer as a non-toxic and efficient gene delivery carrier", *Biomaterials*, 28(11):2061-7 (2007). (abstract only).

Kinosaki, et al., "Identification of heparin-binding stretches of a naturally occurring deleted variant of hepatocyte growth factor (dHGF)", *Biochim Biophys Acta*, 1384(1):93-102 (1998).

Kohn, "New approaches to biomaterials design", *Nat Mater*, 3(11):745-7 (2004). (abstract only).

Kuhl and Griffith-Cima, "Tethered epidermal growth factor as a paradigm for growth factor-induced stimulation from the solid phase", *Nat Med*, 2(9):1022-7 (1996). (abstract only).

Langer and Peppas, "Advances in biomaterials, drug delivery, and bionanotechnology", *AIChE Journal*, 49(12):2990-3006 (2004). (abstract only).

Langer and Tirrell, "Designing materials for biology and medicine", *Nature*, 428(6982):487-92 (2004). (abstract only).

Langer, "Drug delivery and targeting.", *Nature*, 392(6679 Suppl):5-10 (1998). (abstract only).

Luo and Saltzman, "Synthetic DNA delivery systems", *Nat Biotechnol*, 18(1):33-7 (2000). (abstract only).

Luo and Shoichet, "A photolabile hydrogel for guided three-dimensional cell growth and migration", *Nat Mater*, 3(4):249-53 (2004). (abstract only).

Lutolf and Hubbell, "Synthetic biomaterials as instructive extracellular microenvironments for morphogenesis in tissue engineering", *Nature Biotech*, 23(1):47-55 (2005). (abstract only).

Lynn and Langer, "Degradable poly β-amino esters): synthesis, characterization, and self-assembly with plasmid DNA", *J. Am. Chem. Soc.*, 122(44):10761-10768 (2000). (abstract only).

Massia and Hubbell, "Vascular endothelial cell adhesion and spreading promoted by the peptide REDV of the IIICS region of plasma fibronectin is mediated by integrin alpha 4 beta 1." *J. Biol. Chem.*, 267(20):14019-26 (1992). (abstract only).

McRae and Dahlstroem, "Transmitter-loaded polymeric microspheres induce regrowth of dopaminergic nerve terminals in striata of rats with 6-OH-DA induces parkinsonism", *Neurochem Int*, 25(1):27-33 (1994). (abstract only).

Park, et al., "Degradable polyethylenimine-alt-ppoly(ethylene glycol) copolymers as novel gene carriers", *J Control Release*, 105(3):367-80 (2005). (abstract only).

Patel, et al., "Spatially controlled cell engineering on biodegradable polymer sufaces.", *FASEB J.*, 12(14):1447-54 (1998).

Ranieri, et al., "Neuronal cell attachment to fluorinated ethylene propylene films with covalently immobilized laminin oligopeptides YIGSR and IKVAV.II.", *J Biomed Mater Res*, 29(6):779-85 (1995). (abstract only).

Sakiyama-Elbert and Hubbell, "Development of fibrin derivatives for controlled release of heparin-binding growth factors", *J Control Release*, 65(3):389-402 (2000). (abstract only).

Sanclimens, et al., "Synthesis and screening of a small library of proline-based biodendrimers for use as delivery agents", *Biopolymers*, 80(6):800-14 (2005). (abstract only).

Sanghvi, et al., "Biomaterials functionalization using a novel peptide that selectively binds to a conducting polymer", *Nat Mater*, 4(6):496-502 (2005). (abstract only).

Schense, et al., "Enzymatic incorporation of bioactive peptides into fibrin matrices enhances neurite extension", *Nat Biotechnol*, 18(4):415-9 (2000). (abstract only).

Schmidt and Leach, "Neural tissue engineering: strategies for repair and regeneration", *Annu Rev Biomed Eng*, 5:293-347 (2003). (abstract only).

Schmieder, et al., "Development of novel poly(ethylene glycol)-based vehicles for gene delivery", *Biotechnol Bioeng*, 96(5):967-76 (2007). (abstract only).

Silva, et al. "Selective differentiation of neural progenitor cells by high-epitope density nonofibers", *Science*, 303(5662):1352-5 (2004). (abstract only).

Sloots and Weis, "Recombinant derivatives of the human high-mobility group protein HMGB2 mediate efficient Nonviral gene delivery", *FEBS J*, 272(16):4221-36 (2005).

Thomas and Klibanov, "Non-viral gene therapy: polycation-mediated DNA delivery", *Appl Microbiol Biotechnol*, 62(1):27-34 (2003). (abstract only).

Thomas, et al., "Full deacylation of polyethylanimine dramatically boosts its gene delivery efficiency and specificity to mouse lung", *Proc Natl Acad Sci USA*, 102(16):5679-84 (2005).

Van Heest and Tirrell, "Protein-based materials, toward a new level of structural control", *Chem Commun (Chamb)*, 19:1897-904 (2001). (abstract only).

Wagner, "Strategies to improve DNA polyplexes for in vitro gene transfer: will "artificial viruses" be the answers?", *Pharm Res*, 21(1):8-14 (2004). (abstract only).

Wang, et al., "A tough biodegradable elastomer", *Nat Biotechnol*, 20(6):602-6 (2002).

Wender, et al., "The design, synthesis, and evaluation of molecules that enable or enhance cellular uptake: peptoid molecular transporters", *Proc Natl Acad Sci USA*, 97(24):13003-8 (2000).

Zaric, et al., "Effective polyethylenimine-mediated gene transfer into human endothelial cells", *J Gene Med*, 6(2):176-84 (2004). (abstract only).

Zhang, "Fabrication of novel biomaterials through molecular self-assembly", *Nat Biotechnol*, 21(10):1171-8 (2003). (abstract only).

Zhang, et al., "siRNA-containing liposomes modified with polyarginine effectively silences the targeted gene", *J Control Release*, 112(2):229-39 (2006). (abstract only).

* cited by examiner

BIOMIMETIC POLYMERS AND USES THEREOF

CROSS REFERENCE TO RELATED APPLICATIONS

This application is a filing under 35 U.S.C. § 371 of PCT/US2007/072946 filed with the U.S. Receiving Office of the Patent Cooperation Treaty on Jul. 6, 2007, and claims priority to and benefit of U.S. Provisional Application No. 60/819,219 filed on Jul. 7, 2006 by Yadong Wang, and where permissible is incorporated by reference in its entirety.

STATEMENT REGARDING FEDERALLY SPONSORED RESEARCH

This invention was made with Government Support under Agreement R21-EB008565-01A1, awarded by the National Institutes of Health. The Government has certain rights in the invention.

BACKGROUND

The use of synthetic polymers in medicine during World War II marked the beginning of biomaterials science. These materials enabled many new medical treatments that benefited tens of millions of people annually. The advancement of modern medicine demands materials with biological functions, which are lacking in most of the current biomaterials in clinical use. Proper physiological functions rely on a diverse array of materials, the main building blocks of which are amino acids. Numerous bioactivities rely on the versatile amino acid side chains. Further, amino acid derivatives such as dopamine and serotonin are vital signaling molecules in biological processes. Current approaches to functional biomaterials including protein engineering and self-assembled synthetic polypeptides have limited diversity in material properties and functions (most of these polypeptides are hydrogels). Combinatorial chemistry can greatly increase material diversity; however this strategy has yet to be applied to biomolecules. The resulting biomolecules can be used in a variety of applications, including but not limited to medical treatments.

State-of-the-art medical treatments still have limited success in restoring functions to nervous systems after a major assault. A promising solution to this challenge is to induce neurite sprouting and guide the regenerating nerve by appropriately-designed biomaterials. Biomimetic polymers with proper information content and functionality can direct appropriate cellular responses. One way to achieve biomimicry is to integrate biomolecules into polymers. Surface-tethered neurotransmitters can activate the corresponding cellular receptors and neurotransmitters directly integrated into a biomimetic polymer can induce specific responses from neurons.

Numerous materials have been employed to promote nerve regeneration, with properties that range from hydrophobic to hydrophilic, degradable to non-degradable, resistant to protein adsorption to protein-based, and soft to hard. These materials often use laminin epitopes, such as Ile-Lys-Val-Ala-Val (SEQ ID NO:1), to enhance neuron adhesion and sprouting. Because neural activities are highly regulated by neurotransmitters, integrating them into materials may impart bioactivity to synthetic polymers and render them biomimetic. Such biomaterial may lead to an alternative approach to nerve regeneration.

Therefore, it is an object of the invention to provide biomimetic polymers, particularly biodegradable biomimetic polymers.

It is another object to provide biomimetic polymer matrices.

It is still another object to provide biomimetic polymers for use in tissue engineering.

It is a further object to provided matrices for delivery of bioactive factors.

It is yet another object to provide compositions and methods for promoting wound healing and cell differentiation.

It is a further object to provide biomimetic polymers for delivering therapeutic agents including nucleic acids and growth factors.

SUMMARY

Biodegradable polymers incorporating biomolecules are provided. Exemplary polymers are formed by polymerizing biomolecules having a functional group such as a primary amine with diglycidyl esters. One embodiment provides a polymer according to the following formula:

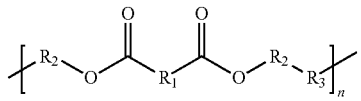

wherein $R_1$ is any alkyl, cycloalkyl, heterocycloalkyl, aryl, heteroaryl, or heterocycle optionally substituted with halide, alcohol, ether, thioether, tertiary amine, ketone, ester, and amide;

$R_2$ is any alkyl, cycloalkyl, aryl, heteroaryl, optionally substituted with halide, alcohol, ether, thioether, tertiary amine, ketone, ester, and amide;

$R_3$ is a biomolecule bound to $R_2$ via an amine bound; and $n$ is $\geq 1$.

In other embodiments, n>than 1,000, greater than 10,000 or even greater than 1,000,000.

In still other embodiments $R_1$ can be polyethylene glycol, $(CH_{12}-CH_2-O-)_x$, where $x \geq 1$ and less than 10,000.

The polymers can be tailored for specific functions and uses by selecting specific biomolecules to be incorporated into the polymer. For example, neurotransmitters such as dopamine can be polymerized with diglycidyl esters to produce biodegradable polymers that stimulate or promote neurite growth or outgrowth. Polymers incorporating neurotransmitters can be used for treating neurological disorders.

Another embodiment provides biodegradable polymers that serve as a delivery vehicle for nucleic acids. Arginine monomers can be polymerized with diglycidyl esters to produce polymers that carry a net positive charge under physiological conditions. The positively charged polymer can interact with negatively charged nucleic acids to assist in delivering the nucleic acid to a cell. In certain aspects, the polymer includes a protein transduction domain or cell penetrating peptide.

Still another embodiment provides biodegradable polymer matrix. The matrix can be formed by combining the disclosed polymers with heparin sulfate. The matrix can also contain bioactive factors bound or trapped in the matrix which can be released from the matrix when the matrix is administered to a host, for example when applied to a wound.

DETAILED DESCRIPTION

I. Definitions

Figure 1A:
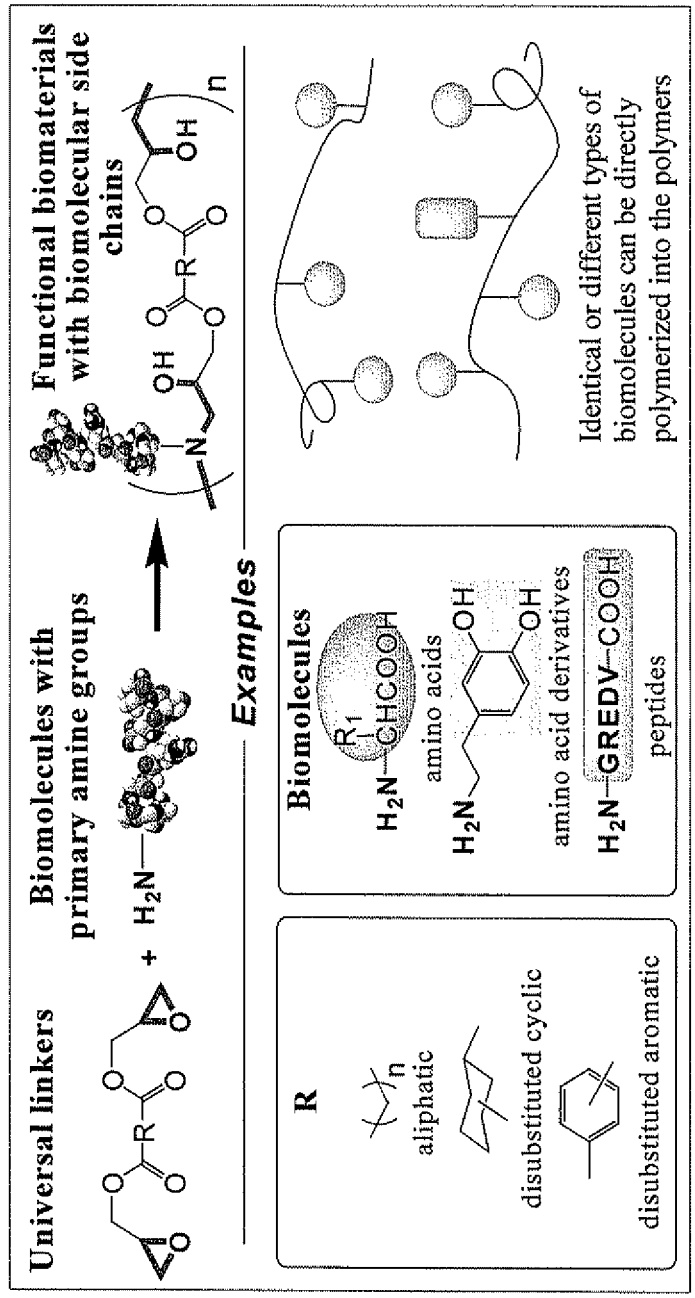
FIG. 1A shows exemplary functional biomaterials with degradable backbones and biomolecular side chains. The linkers can be synthesized from essentially any dicarboxylic acids enabling further control of properties such as hydrophilicity, structural rigidity, and spacing of biomolecules.

As used herein, the term "alkyl group" is intended to mean a straight- or branched-chain monovalent radical of saturated and/or unsaturated carbon atoms and hydrogen atoms, such as methyl (Me), ethyl (Et), propyl, isopropyl, butyl, isobutyl, t-butyl, ethenyl, propenyl, butenyl, pentenyl, ethynyl propynyl, butynyl, pentynyl, hexynyl, and the like, which may be unsubstituted (i.e., containing only carbon and hydrogen) or substituted by one or more suitable substituents as defined below (e.g., one or more halogens, such as F, Cl, Br, or I, with F and Cl being preferred). A "lower alkyl group" is intended to mean alkyl group having from 1 to 4 carbon atoms in its chain.

The term "biomolecule" refers to naturally produced molecules found in nature having one or more carbon atoms, including polymeric or nonpolymeric molecules. Representative biomolecules, include but are not limited to amino acids, nucleotides, purines, pyrimidines, lipids, carbohydrates, vitamins, proteoglycans, or combinations thereof.

A "cycloalkyl group" is intended to mean a non-aromatic monovalent monocyclic, bicyclic, or tricyclic radical containing 3, 4, 5, 6, 7, 8, 9, 10, 11, 12, 13, or 14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more substituents.

A "heterocycloalkyl group" is intended to mean a non-aromatic monocyclic, bicyclic, or tricyclic alkane, which is saturated or unsaturated, containing 3, 4, 5, 6, 7, 8, 9, 10, 11, 12, 13, 14, 15, 16, 17, or 18 ring atoms, which includes 1, 2, 3, 4, or 5 heteroatoms selected from nitrogen, oxygen, and sulfur, where the alkane is unsubstituted or substituted by one or more suitable substituents as defined below, and to which may be fused one or more cycloalkyl groups, aryl groups, or heteroaryl groups, which themselves may be unsubstituted or substituted by one or more appropriate substituents.

An "aryl group" is intended to mean an aromatic monocyclic, bicyclic, or tricyclic alkane containing 6, 10, 14, or 18 carbon ring atoms, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents.

A "heteroaryl group" is intended to mean an aromatic monocyclic, bicyclic, or tricyclic alkane containing 4, 5, 6, 7, 8, 9, 10, 11, 12, 13, 14, 15, 16, 17, or 18 ring atoms, including 1, 2, 3, 4, or 5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents.

A "heterocycle" is intended to mean a heteroaryl or heterocycloalkyl group (each of which, as defined above, are optionally substituted).

II. Biomimetic Polymeric Compositions and Matrices

Figure 1B:
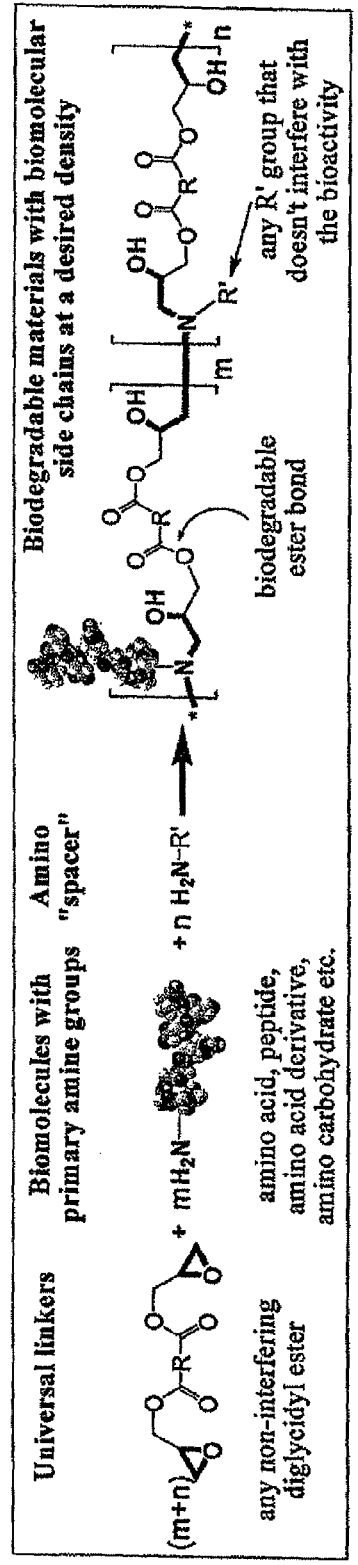
FIG. 1B shows a diagram indicating that the density of the biomolecules can be controlled by copolymerization with an "inert" primary amine.

One embodiment provides a platform for an extensive library of functional polymeric biomaterials with biomolecular side chains. The integration of a large variety of biomolecules including amino acids and derivatives confers a wide range of biological functions to the polymers, which may create a broad impact in biomedicine. The disclosed materials can be used for numerous applications including, but not limited to tissue engineering, wound repair, nerve repair, nerve regeneration, and drug delivery. The disclosed compositions can be produced by polymerizing virtually any biomolecules containing a primary amine group with diglycidyl esters. Diverse biomolecules such as amino acids, peptides, lipids and carbohydrates and their derivatives bestow a whole spectrum of biological functions to these novel materials, while the hybrid nature of the polymers incur a lower cost than materials like synthetic polypeptides (FIG. 1). Exemplary poly(aminoglycerol esters) (PAGE) have an ester backbone and biomolecular side chains. Copolymerization of different types of biomolecules will further increase the diversity of these materials. Further, the density of the biomolecules can be controlled by copolymerization with an "inert" primary amine.

In one embodiment, the molecular design is a result of four deliberations: (1) biodegradability: degradable material is favored because it will be absorbed by the body so as not to constrict the regenerating nerve; (2) degradable functional group: for example esters for versatile synthesis; (3) the polymerizable biomolecular functional group, for example a primary amine because of its ubiquitous presence among key biomolecules, secondary amines and alcohol groups can also be used; (4) polymerization mechanism, for example Michael Addition due to its mild reaction conditions. The R in the linkers can be synthesized from essentially any dicarboxylic acids enabling further control of the properties such as hydrophilicity, structural rigidity, and spacing of biomolecules. Representative dicarboxylic acids include, but are not limited to adipic acid, aldaric acid, aspartic acid, azelaic acid, camphoric acid, dimercaptosuccinic acid, fumaric acid, glutamic acid, glutaric acid, isophthalic acid, itaconic acid, ketoglutaric acid, maleic acid, malic acid, malonic acid, mesoxalic acid, n-acetylglutamic acid, oxalic acid, oxaloacetic acid, phthalic acid, phthalic acids, pimelic acid, sebacic acid, suberic acid, succinic acid, tataric acid, terephthalic acid, traumatic acid, dodecanedioic acid, chaetomellic acids, ceriporic acids, 1,2-cyclohexane biacarboxylic acid, 1,4-cyclohexane biacarboxylic acid, substituted dicarboxylic acids, and combinations thereof. The R group can also have other function groups if necessary. The biomolecules that render the resultant polymer bioactive can be any biologically important molecules that have a primary amine group ($NH_2$). Examples include amino acid, amino acid derivatives, peptides, amine-containing carbohydrates, neurotransmitters, and alkaloids. Polymers synthesized using this platform can have a wide range of properties/functions because of the wide range of monomers. This enables the biomaterials to be tailored for a specific application.

One embodiment provides a polymer according to the following formula:

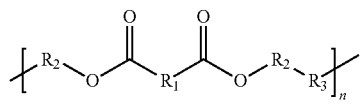

wherein $R_1$ is any alkyl, cycloalkyl, heterocycloalkyl, aryl, heteroaryl, or heterocycle optionally substituted with halide, alcohol, ether, thioether, tertiary amine, ketone, ester, and amide.

$R_2$ is any alkyl, cycloalkyl, aryl, heteroaryl, optionally substituted with halide, alcohol, ether, thioether, tertiary amine, ketone, ester, and amide;

$R_3$ is a biomolecule bound to $R_2$ via an amine bound; and n is $\geq 1$.

In other embodiments, n>than 1,000, greater than 10,000 or even greater than 100,000.

Another embodiment provides a polymer according to the following formula:

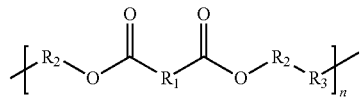

wherein $R_1$ is $C_2$-$C_8$ alkyl, cycloalkyl, heterocycloalkyl, aryl, heteroaryl, or heterocycle optionally substituted with OH or halide;

$R_2$ is $CH_2$—$CH(OH)$—$CH_2$;

$R_3$ is a biomolecule bound to $R_2$ via an amine bound; and n >1.

In other embodiments, n >than 1,000, greater than 10,000 or even greater than 100,000.

A. Synthesis of the Monomers

In one embodiment, the synthesis of diglycidyl esters from dicarboxylic acids has been optimized, for example to a typical overall yield of 91%. The examples of esters synthesized are listed in Scheme 1.

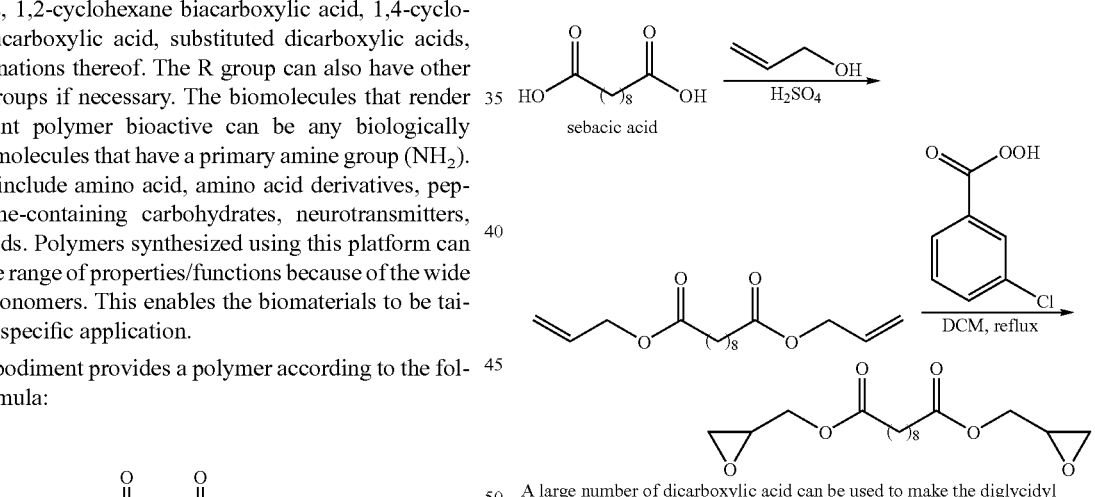

Scheme 1.
High yield synthesis of diglycidyl esters from dicarboxylic acids.

A large number of dicarboxylic acid can be used to make the diglycidyl esters using the above synthesis method. We have applied this strategy to the following acids to illustrate the wide range of possibilities:

succinic acid

1,2-cyclohexane biacarboxylic acid

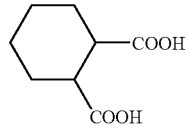

1,4-cyclohexane biacarboxylic acid

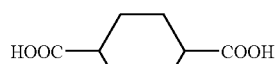

teraphthalic acid

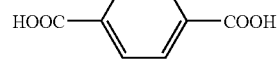

Compounds used to polymerize biomolecules can be modified to have a functional group on either end of the molecule. Epoxide functional groups are illustrated in the diglycidyl esters above, but it will be appreciated that other functional groups can be used provided the functional groups react with a biomolecule, for example with a primary amine to form a polymer. For example, other functional groups include but are not limited to carbonyl containing groups, aldehydes, carboxylic acids, esters, acid-chlorides, alkyl halides, etc.

B. Neurotransmitter-Based Biomaterials for Nerve Regeneration

1. Biomimetic Polymers Incorporating Dopamine

Biomaterials are widely used in disease treatment and improving human well-being. Recently, significant advances have been made to impart biological activity to biomaterials. Most of the existing bioactive materials are derived from extracellular matrix (ECM) or are modified with ECM motifs. The most widely used ECM motifs include protein epitopes such as Arg-Gyl-Asp (RGD), Tyr-Ile-Gly-Ser-Arg (YIGSR) (SEQ ID NO:2), and Ile-Lys-Val-Ala-Val (IKVAV) (SEQ ID NO:1); and glycosaminoglycans such as heparin. In addition to cell-ECM interactions, cell differentiation and survival also depend on constant interactions with other cells through a plethora of messenger molecules. In one embodiment, the biomaterial design strategy uses chemical messengers as monomers to impart bioactivities to the resultant biodegradable polymers. To demonstrate the potential of this approach, a material based on the neurotransmitter dopamine was produced. The resultant biomaterial promotes neurite growth more vigorously than laminin, poly(D-lysine) (PDL), and a tyrosine-based polymer. Other bioactive agents that can be polymerized include glutamate, aspartate, histamine, norepinephrine, serotonin, taurine, glycine and 4-aminobutyrate, and neuropeptides such as methionine enkephalin.

In addition to repair nerve injury, these biomaterials can also be used to differentiate embryonic or adult stem cells. In one embodiment, the biomaterials can promote differentiation of embryonic or adult stem cells into neurons because many neurotransmitters are expressed at high concentrations in the embryonic development of nervous tissues. These could serve as a valuable cell source for treatment of neurodegenerative diseases. Furthermore, multiple types of neurotransmitters can be integrated in a single material, as neurons are known to express receptors for multiple neurotransmitters. Thus, one embodiment provides a polymeric biomaterial having at least two different bioactive factors that have a primary amine as a monomer. For example, the biodegradable polymer can include at least two bioactive factors selected from the group consisting of dopamine, glutamate, aspartate, histamine, norepinephrine, serotonin, taurine, glycines, 4-aminobutyrate, and methionine enkephalin.

For all these materials, the density of the bioactive factor can be controlled by copolymerizing with an inert amine such as n-butylamine, leucine ethyl ester, and other simple amines, simple amino acids, or simple aminocarbohydrates such as glucosamine. The synthesis of one such copolymer is illustrated in FIG. 1.

Neurotransmitters, messengers in neural communication, are essential in neuronal outgrowth during embryonic and neonatal development and after injury. The depletion of neurotransmitters during embryonic development results in developmental defects of the brain, suggesting that neurotransmitters play crucial roles as morphogens or neurotrophic factors. Dopamine in particular is vital in axon growth and synapse formation during the embryonic stage. A biocompatible material containing neurotransmitter functional groups should promote axon growth. Specific design parameters address the following criteria: (1) degradability, a degradable material is advantageous because prolonged presence of an implant may compress or hinder regenerating nerves; (2) degradable functional groups, for example esters for their versatile synthesis; (3) dopamine functional groups to be polymerized, for example, the primary amine because the catechol is preserved among the catecholamine neurotransmitters whereas the amine group can be alkylated as in epinephrine; (4) polymerization mechanism, for example between dopamine and an epoxide because it alkylates the amines under mild conditions. A representative polymer is synthesized from 1,2-cyclohexyldiglycidyl ester and dopamine, hence the abbreviation—PCD (Scheme 2). The polymer backbone has biodegradable ester bonds and carries positive charges, known to increase cell adhesion. The diglycidyl ester can be synthesized from virtually any dicarboxylic acid allowing control of the property of the polymer backbone. The concentration of neurotransmitter functional groups in the polymer can be adjusted by copolymerization with a spacer allowing further control of the structure and function of the biomaterials.

2. Biomimetic Polymers Incorporating Acetylcholine-Like Moieties

Acetylcholine is a chemical messenger widely studied for its role in synaptic transmission of an action potential and is known to regulate neuronal cytoarchitecture in embryonic and adult neurons. The activation of acetylcholine receptors induces neurite outgrowth and may promote the formation and strengthening of synapses. Acetylcholine-mediated axonal growth is believed to occur via an increase in intracellular calcium level, which likely initiates intracellular signaling events. This is supported by the observation that stimulating acetylcholine receptors triggers the influx of extracellular calcium and activates specific gene transcription. One of the activated genes is actin, which plays a key role in axon extension. Additionally, acetylcholine administration affects the direction of neurite growth. Local application of the neurotransmitter induces the nerve growth cone to turn toward the acetylcholine gradient and the spontaneous release of acetylcholine from embryonic neurons suggests its potential role in pathfinding during synapse formation. Because of its roles in regulating neuronal development, affecting neurite growth, and guiding the nerve growth cone, acetylcholine may be used to elicit and direct nerve regeneration after injury.

One embodiment provides a polymer produced using 2-aminoethyl acetate with diglycidyl sebacate (see Scheme 1, resultant polymer abbreviated as PSA). Another embodiment provides a polymer synthesized using 1,2-cyclohexyldiglycidyl ester (resultant polymer abbreviated as PCA). The polymers can be used to promote neurite growth, nerve regeneration, and in the treatment of neurological disorders.

C. Nucleic Acid Delivery Vehicles

DNA and RNA are potential therapeutic agents that may transform human disease treatment. Unprotected nucleic acids are rapidly degraded in the body. Thus a delivery strategy is required to prolong the half-life of therapeutic nucleic acids. Viral vectors have great delivery efficiency, but safety concerns may limit their clinical utility. While properly designed nonviral vectors are safe, they typically have low transfection efficiency. Arginine plays a key role in nucleic acid condensation and cellular uptake, two essential steps in the delivery of genetic materials. DNA binding proteins, histones and protamines, use arginine and lysine to bind DNA. Furthermore, an 11 amino acid epitope (YGRKKRRQRRR) (SEQ ID NO:3) of HIV Tat protein, known to transport exogenous molecules across cell membranes, contains 6 arginines. One embodiment provides an arginine-based PAGE integrated with Tat epitope having improved the transfection efficiency of nucleic acids. Compared with non-degradable vectors such as PEI, PAGE is likely less toxicity. The relative ratio of arginine and Tat epitope in the polymer can be adjusted to achieve optimal transfection efficiency.

Another embodiment provides arginine based polymers PSR and PCR synthesized using diglycidyl succinate (see Scheme 3) and 1,2-cyclohexyldiglycidyl ester respectively. The polymers can form complexes with nucleic acids including, but not limited to, plasmid DNA and SiRNA.

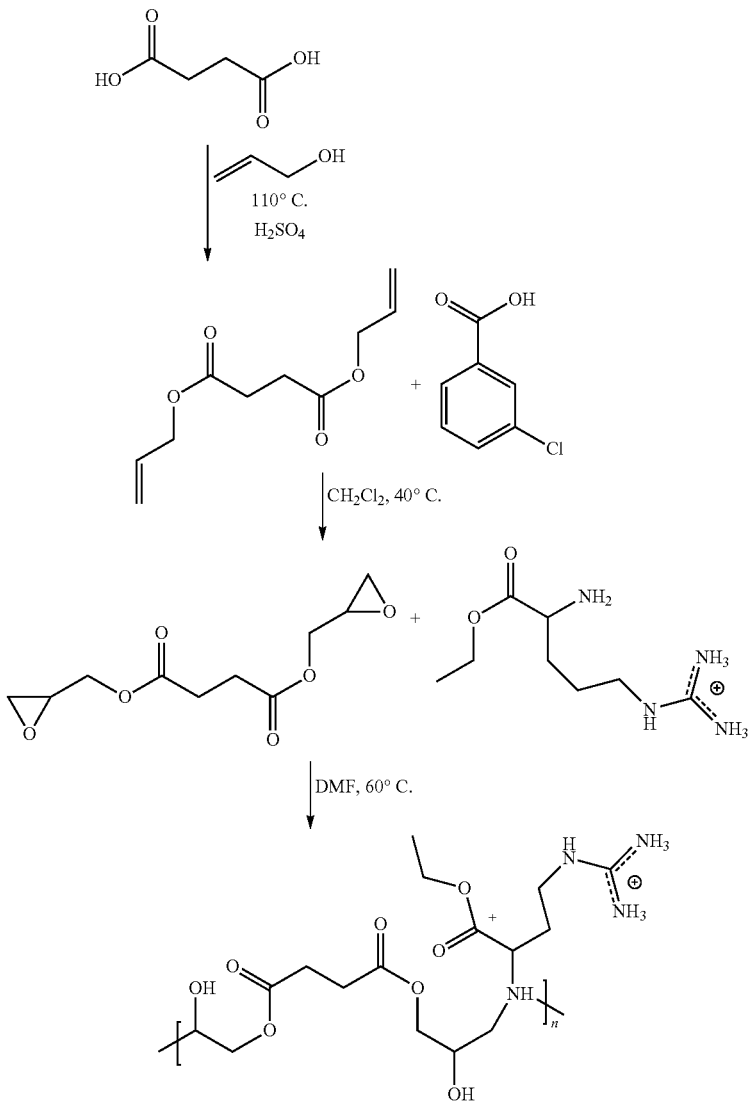

Scheme 3: Production of Arginine Based Polymer PSR

D. Cardiovascular Tissue Engineering

Coronary artery disease is the leading cause of mortality and disability in the US and other industrialized countries. Current vascular grafts have limited success, especially for small arteries like the coronary arteries. Tissue engineering may produce small arteries that are mechanically compliant, vasoresponsive, and antithrombogenic (resist blood clot formation). Tissue engineered small arteries can already match the strength of native vessels, but antithrombogenicity remains elusive. Endothelial cells (ECs) cover the lumen of a blood vessel to provide antithrombogenicity in healthy vasculature. Selective binding to ECs is critical to ensure antithrombogenicity as adhesion of other blood cells such leukocytes and platelets promotes thrombosis. A plasma fibronectin epitope is known to selectively bind EC even at low surface density (10 pmol/cm$^2$)

Another embodiment provides biomimetic polymers incorporating YIGSR (SEQ ID NO:2) or IKVAV (SEQ ID NO:1) as the biomolecules. It will be appreciated that more than one type of biomolecules can be incorporated in to a polymer. Additionally, the biomolecules can be selected

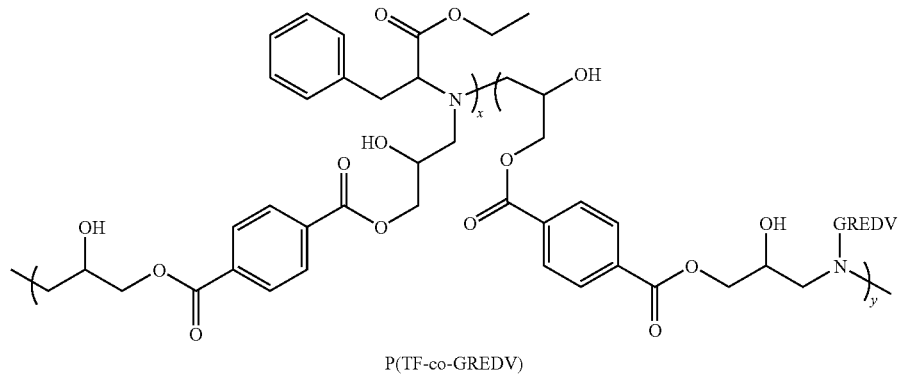

P(TF-co-GREDV)

Figure 7:
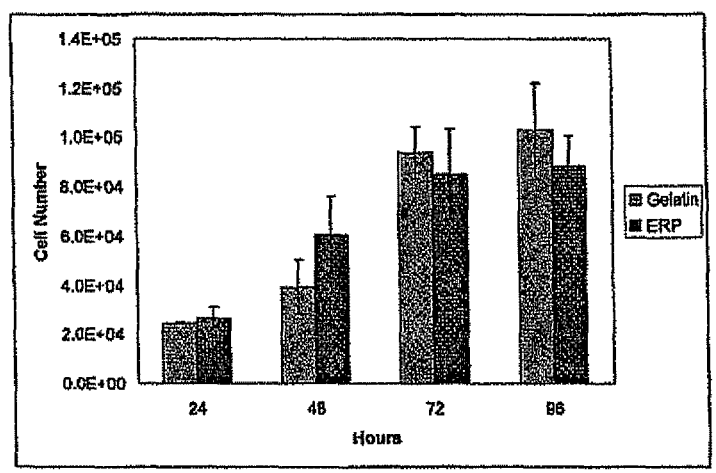
FIG. 7 is a bar graph showing the proliferation of BaEPCs on gelatin-coated and P(TF$_{90}$-co-GREDV$_{10}$)-coated surfaces were similar as determined by MTT assay. Data expressed as mean±SD.
Figure 8:
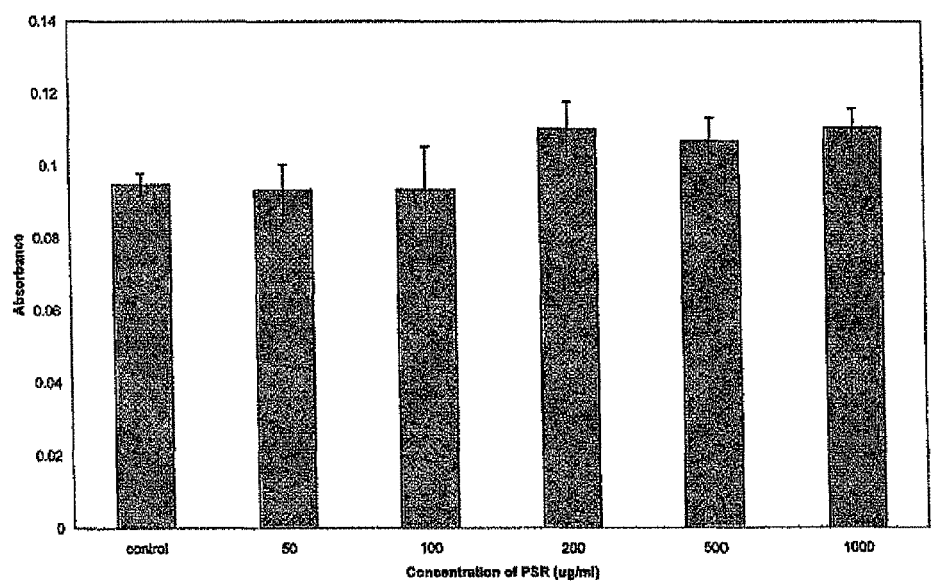
FIG. 8 are bar graphs showing results of gel retardation assay which indicate complete retardation of plasmid DNA at N/P ratio between 4/1-8/1. From left to right: naked DNA, 4/1, 8/1, 12/1, and 16/1 N/P ratios.

GREDV (SEQ ID NO:4), wherein the amino end of glycine will be polymerized was used. GREDV (SEQ ID NO:4) was polymerized with diglycidyl terephthalate. The resultant polymer, P(TF-co-GREDV$_{100}$), was characterized using FTNMR and FTIR (FIG. 7). The epitope has been copolymerized with 'inert' amino compounds including but not limited to glycine ethyl ester and phenylalanine ethyl ester to test the low limit of eptiope concentration for function and high limit of eptiope concentration that inhibits cell migration. The structure of one such polymers, P(TF-co-GREDV), a copolymer of phenylalanine ethyl ester, GREDV (SEQ ID NO:4), and diglycidyl terephthalate is illustrated above. Baboon endothelial progenitor cells (BaEPCs) displayed normal morphology and phenotypic expression of von Willebrand factors (vWF) and proliferated well on P(TF$_{90}$-co-GREDV$_{10}$) (FIG. 8). BaEPC adhesion weakened in the presence of 40 fmol/ml GREDV (SEQ ID NO:4) dissolved in medium indicating that GREDV (SEQ ID NO:4) is the functional group that promoted EC adhesion.

The adhesion strength between P(TG$_{90}$-co-GREDV$_{10}$) [glycine ethyl ester as the spacer (90%), GREDV (SEQ ID NO:4) (10%) terephthalate backbone] and endothelial cells under arterial sheer stress was quantitatively evaluated. To save the consumption of baboon EPCs, human umbilical vein endothelial cells (HUVECs) were used as a model of EPCs. HUVECs adhere to the polymer surfaces well and arterial shear stress resulted in minimal cell detachment. The polymer surfaces were conditioned in M199 media overnight and washed with DPBS before plating HUVECs. Cells were allowed to adhere for four hours before starting shear conditions in a parallel plate flow chamber. Microscopy of the cells indicated that they remained attached to the surface after 1 hour of 40 dynes/cm$^2$ laminar shear stress.

Thus, the disclosed biomimetic polymers can be used to engineer endothelial cells to vascularize tissue or organs. This polymer or its analogs can also be used to coat any surfaces that needs to be endothelialized such as stents and other blood contacting surfaces. This polymer itself can be used to form devices that contacts bloods.

depending on the tissue to be treated. For example, neuronal biomolecules can be incorporated into polymers for treating nervous tissue.

E. Matrices and Growth Factors

1. Matrix Materials

Growth factors play an important role in regulating the body functions in healthy and diseased states. A controlled delivery of growth factors can significantly increase the half life and thus bioavailability of the growth factors. Many growth factors are stored in the heparin-bound state and released when the body needs them. Heparin is heavily negatively charged. One embodiment provides poly-cations conjugated to [heparin:growth factor] complexes as a way to control the release of the growth factors.

Matrices using the disclosed biomimetic polymers can be formed by crosslinking ionically, covalently or by combinations thereof, one or more polymeric materials to form a polymeric matrix. Alternatively the matrices can be formed by entangling polymeric fibers. In certain embodiments the matrices are formed having sufficient inter-polymer spacing to allow for ingrowth or migration of cells into the matrix.

One embodiment provides a matrix formed by one or more of the disclosed biomimetic polymers. In certain other embodiments, the matrix is formed by one or more of the disclosed biomimetic polymers and a second polymer. The second polymer can be natural or synthetic. Suitable natural polymers include, but are not limited to proteins and polysaccharides. The most preferred protein is fibrin, although other proteins such as collagen and gelatin can also be used. Polysaccharides and glycoproteins may also be used. In some embodiments, it is also possible to use synthetic polymers which are crosslinkable by ionic or covalent binding.

The matrix material is preferably biodegradable by naturally present enzymes. The rate of degradation can be manipulated by the degree of crosslinking and the inclusion of protease inhibitors in the matrix.

2. Degradable Linkages

The polymers forming the matrix can be modified to include one or more degradable linkages. When protein polymers are included, enzyme cleavage sites can be included, such as the site for cleavage by thrombin. These sites may be degradable either by non-specific hydrolysis (i.e., an ester bond) or they may be substrates for specific enzymatic (either proteolytic or polysaccharide degrading) degradation. These degradable sites allow the engineering of more specific release of bioactive factor from the matrices. For example, degradation based on enzymatic activity allows for the release of bioactive factors to be controlled by a cellular process rather than by diffusion of the factor through the matrix.

The degradation sites allow the bioactive factor to be released with little or no modification to the polymer, which may result in higher activity of the factor. In addition, it allows the release of the factor to be controlled by cell specific processes, such as localized proteolysis, rather than diffusion from some porous materials. This allows factors to be released at different rates within the same material depending on the location of cells within the material. Cell specific proteolytic activity is vital in applications such as nerve regeneration, which occur over long periods of time. This also reduces the amount of total growth factor needed, since its release is controlled by cellular processes. Conservation of growth factor and its bioavailability are distinct advantages of exploiting cell specific proteolytic activity over the use of diffusion controlled release devices which characteristically result in the loss of a significant amount of bioactive factor in an initial burst release.

Enzymes that could be used for degradation are numerous. Proteolytically degradable sites could include substrates for collagenase, plasmin, elastase, stromelysin, or plasminogen activators.

3. Heparin; Heparin Binding Peptides

The matrix can be modified through the inclusion of heparin and/or heparin binding fragments, which bind directly or indirectly to proteins which bind to heparin. In the latter case, the peptide can bind to heparin, which is then available for binding to factors which include a heparin binding site, or the peptide can itself contain a heparin portion which is bound by certain heparin-binding growth factors. These can be attached to the matrix material using standard techniques, as discussed in more detail below.

In a preferred embodiment, heparin is incorporated in to the cationic polymer and the [polymer:heparin] matrix is formed. In another embodiment, heparin is attached to the polymeric matrices non-covalently using a two-part system consisting of a peptide chimera and heparin itself. The peptide chimera consists of two domains, a factor XIIIa substrate and binding domain specific for the polymer, in particular the biomolecules incorporated into the polymer. Once the peptide chimera is cross-linked into the polymeric matrix it attaches the heparin (or other polysaccharides) by non-covalent interactions.

4. Bioactive Factors

Many growth factors that are involved in morphogenesis, both in the developing organism and in the adult, bind to extracellular matrix molecules. This affinity provides for a local mode of action of the morphogen, preventing uncontrolled distal influences. The principal matrix affinity interaction that is involved in this localization of influence is for heparin and heparan-sulfate proteoglycans. Growth factors that bind to heparin include the transforming growth factor ("TGF")-beta superfamily (including the bone morphogenic proteins, "BMPs"), the fibroblast growth factor ("FGF") family, and vascular epithelial growth factor ("VEG"), VEG-F, among others. In general, growth factors which are considered to bind heparin will elute from a heparin-affinity column at NaCl concentrations above physiological levels (greater than or equal to 140 mM). Additional"heparin-binding" growth factors include interleukin-8, neurotrophin-6, heparin-binding epidermal growth factor, hepatocyte growth factor, connective tissue growth factor, nerve growth factor, placental growth factor, platelet derived growth factor, insulin like growth factor-1, platelet derived growth factor-BB, interferon-gamma, midkine, hepatocyte growth factor, connective tissue growth factor, and heparin-binding growth associated molecule. These growth factors have been shown to regulate tissue maintenance, growth, and repair.

Heparin-binding domains naturally occur in many different families of growth factors. One of these families with one or more member that bind heparin are the fibroblast growth factors (Presta, M., et al. (1992). Biochemical and Biophysical Research Communications. 185:1098-1107). Additional growth factors which bind heparin include transforming growth factor, bone morphogenetic factor, interleukin-8, neurotrophin-6, vascular endothelial cell growth factor, heparin-binding epidermal growth factor, basic fibroblast growth factor, hepatocyte growth factor, connective tissue growth factor, midkine, and heparin-binding growth associated molecule (Gotz, R., et al., (1994), Nature. 372:266-269; Kaneda, N. et al., (1996) J. Biochem. 119:1150-1156; Kiguchi, K., et al., (1998) Mol. Carcinogensis. 22:73-83; Kinosaki, M., et al., (1998). Biochim. Biophys. Acta. 1384:93-102; McCaffrey, T., et al., (1992) J. Cell. Physiol. 152:430-440; Nolo, R., et al., (1996) Eur. J. Neurosci 8:1658-1665; Spillmann, D., et al., (1998). Journal of Biological Chemistry. 273:15487-15493; Steffen, C., et al. (1998); Growth Factors. 15:199-213. Tessler, S., et al, (1994) J. Biol. Chem. 269:12456-12461). These factors have shown the potential to enhance healing in many different types of tissue including vasculature, skin, nerve and liver. Therefore, these materials can be used with the disclosed polymers and polymer matrices to enhance wound healing in many different parts of the body by selecting the appropriate growth factor and appropriate biomimetic polymer.

5. Incorporation of Biofactors into the Matrices

A simple way to incorporate many bioactive factors of interest in healing and regeneration into the polymer matrices is to include heparin and use the heparin to sequester heparin-binding proteins, such as heparin-binding growth factors. This can be accomplished by forming a nanometer to micrometer scale fibrillar to bead-like matrix that precipitate out of an aqueous medium by charge neutralization between the cationic polymer in and the anionic heparin so that the heparin and the polymer fibers entangle; indirectly by cross-linking a heparin-binding peptide into the polymer matrix and binding heparin to this peptide non-covalently (using a bifunctional peptide containing a heparin-binding domain and polymer binding domain); directly coupling a heparin-peptide chimera (where the heparin is chemically attached to a peptide containing a binding site for the polymer). Regardless of the method of incorporation, the incorporated heparin can then sequester proteins, such as growth factors with heparin binding affinity, in the polymer matrix in a manner similar to the way that they are sequestered to the extracellular matrix in nature. Heparin can also protect these factors from proteolytic degradation and prolong their activity until they are released from the matrix. Heparin can also present the growth factors in their bioactive form, thus greatly increase the efficiency of the therapy.

III. Methods of Use

The disclosed compositions can be used in tissue engineering, wound healing, drug delivery, nucleic acid delivery, and nerve regeneration. In certain aspects, the compositions are combined with a drug, for example a nucleic acid, and are administered to host, for example a mammal. The compositions either alone or in combination with a second therapeutic can be used to treat various pathologies, including but not limited to cancer, diabetes, inflammation, genetic disorders, age-related disorders, nerve degeneration, bone fractures, wounds, and tissue regeneration, Nucleic acids include, but are not limited to RNA, DNA, and combinations thereof. Antisense RNA, antisense DNA, microRNA, siRNA, nucleic acids encoding a peptide or inhibitory nucleic acid can be delivered to a cell or host using the disclosed compositions.

In one embodiment, the disclosed composition is administered to a host at an injury site to promote tissue growth or regeneration. For example, the disclosed compositions can be applied to areas of trauma in the central or peripheral nervous systems or the circulatory system. The compositions can provide a surface or three dimensional scaffold to assist cellular growth in the areas of trauma. In certain embodiments, neural cell or cardiac cell growth is induced relative to controls.

EXAMPLES

Example 1

Synthesis and Characterization of Biomimetic Polymers

Figure 2A:
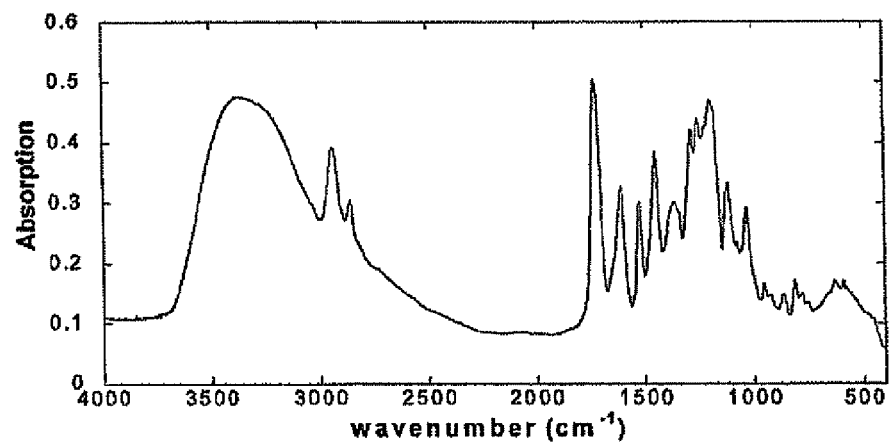
FIGS. 2A-B show absorption spectra of a representative biomaterial produced from 1,2-cyclohexyldiglycidyl ester and dopamine (PCD) and 1,2-cyclohexyldiglycidyl ester and tyrosine (PCY), respectively.
Figure 2B:
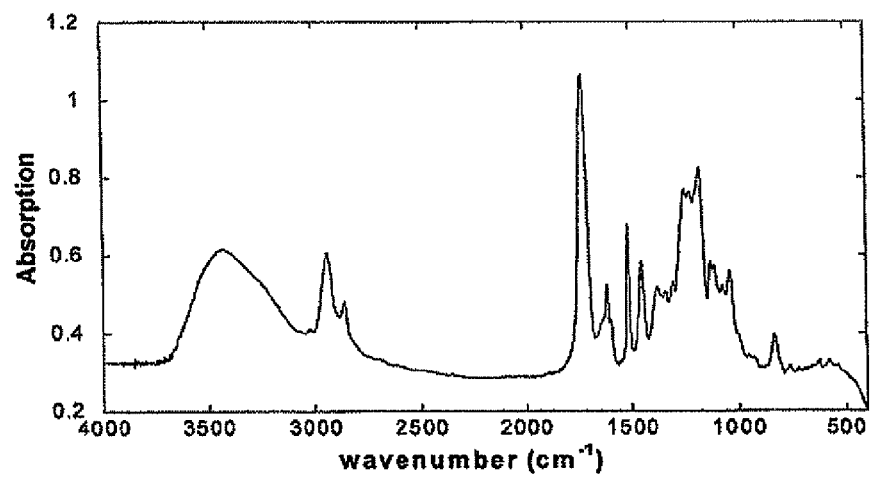

Diglycidyl 1,2-cyclohexanedicarboxylate and dopamine were dissolved in N,N-dimethylformamide (DMF) with an optional 0.1% $Mg(ClO_4)_2$ under $N_2$ with constant stirring. The reaction mixture was heated at 90° C. for 7 days and the resultant viscous liquid was precipitated in ethyl ether. The precipitate was subjected to a quick washed with D.I. water to remove the catalyst and byproducts. The purified PCD (71% yield) was lyophilized and stored under $N_2$ at −40° C. The polymer was soluble in DMF, low molecular weight alcohols and ketones but was insoluble in water. PCD, $^1$H NMR (methanol-$d_4$) δ 6.62-6.55 (br, 3H), 4.18-3.80 (br, 3H), 3.60-3.31 (br, 3H), 3.16-2.98 (br, 2H), 2.90-2.40 (br, 6H), 2.02-1.80 (br, 2H), 1.78-1.61 (br, 2H), 1.49-1.17 (br, 6H). FTIR: 1727 $cm^{-1}$ (ester C=O), 1451 $cm^{-1}$ (C—N), 1289 $cm^{-1}$ (catechol C—O), 814 and 866 $cm^{-1}$ (1,2,4-trisubstituted aromatic ring). The absence of absorption at 1674 $cm^{-1}$, 1662 $cm^{-1}$, and 1564 $cm^{-1}$ that are associated with dopamine-quinone, indicating minimal oxidation of catechol to quinine (FIG. 2A). The molecular weight of PCD was found to be 5,260 as determined by MALDI-MS. When tyrosine ethyl ester was used in lieu of dopamine, PCY was obtained at 92% yield. PCY, $^1$H NMR (methanol-$d_4$) δ 7.09-6.73 (br, 2H), 6.68-6.41 (br, 2H), 4.12-3.61 (br, 7H), 3.58-3.30 (br, 3H), 3.16-2.62 (br, 6H), 2.59-2.37 (br, 2H), 2.08-1.77 (br, 3H), 1.75-1.60 (br, 2H), 1.45-1.14 (br, 5H). FTIR: 1732 $cm^{-1}$ (ester C=O), 1220 $cm^{-1}$ (phenol C-0), 1377 $cm^{-1}$ (phenol O—H in-plane bending), 834 $cm^{-1}$ (para-substituted aromatic ring) (FIG. 2B). PCA, PCR, PSA, and PSR were obtained using similar synthetic methods with the respective monomers. P(TF-co-GREDV) was synthesized similarly except the reaction temperature was 60° C.

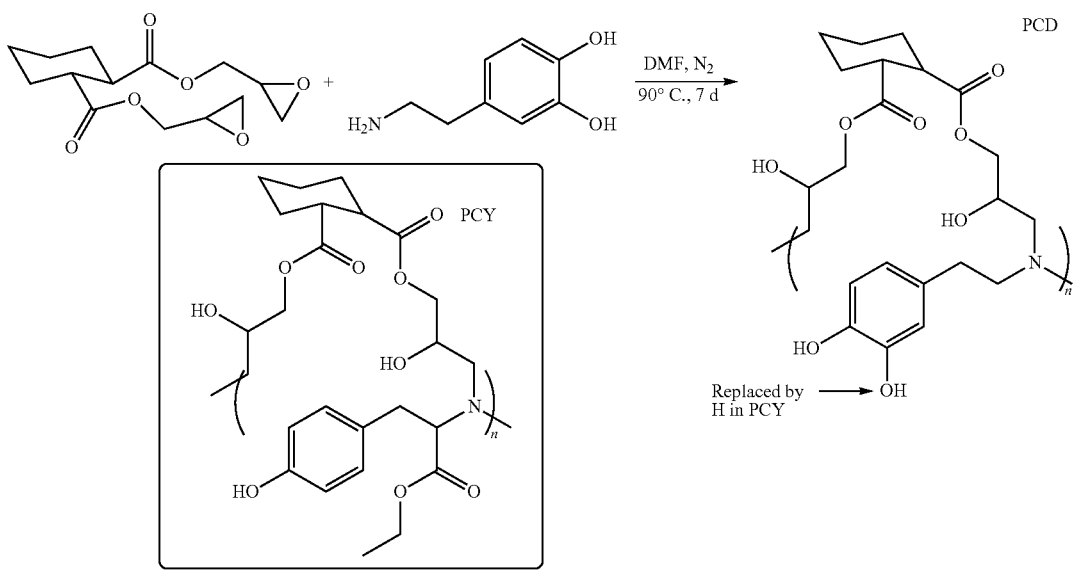

Scheme 2. PCD was synthesized using dopamine as a monomer. This synthesis strategy can be applied to a large number of diglycidyl esters and biomolecules containing primary amines. The key difference between PCD and PCY is the ——OH group of the catechol.

Figure 3:
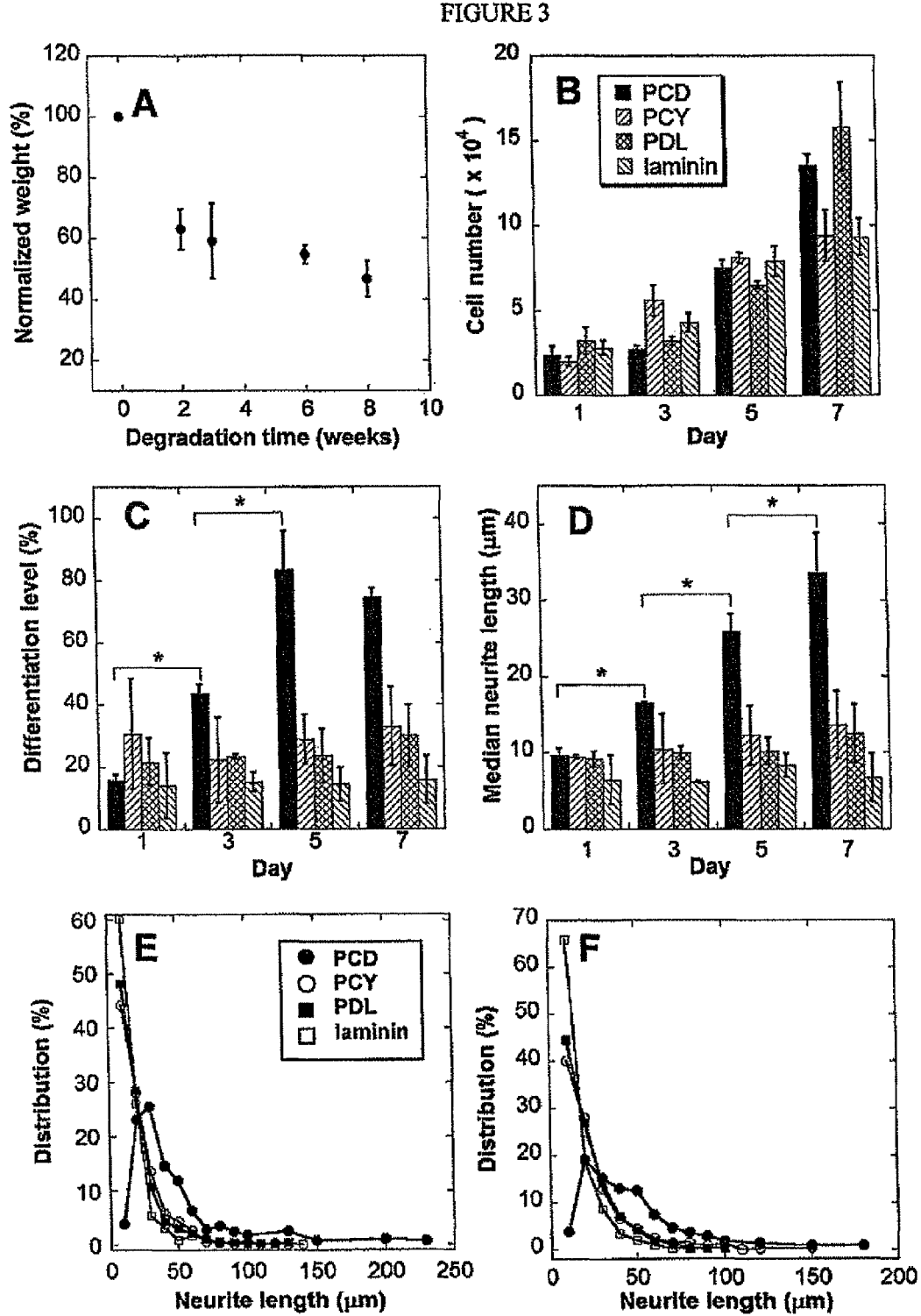
FIG. 3A is a graph showing degradation of PCD polymer expressed as a decrease of mass with time. Data expressed as mean±S.D.
FIG. 3B is a series of bar graphs showing in vitro biocompatibility as indicated by the number of metabolically active cells on PCD relative to the controls.
FIG. 3C is a series of bar graphs showing that cells displayed the highest differentiation level on PCD, and the level increased significantly with time. The controls did not induce more differentiation as the culture time increased.
FIG. 3D is a series of bar graphs showing that the median neurite length increased substantially on PCD over the culture period. In comparison, the change on the control surfaces was statistically insignificant over the entire culture period.
FIG. 3E is a line graph showing the distribution of neurite length on PCD versus the controls at day 5.
FIG. 3F is a line graph showing the distribution of neurite length on PCD versus the controls at day 7. The most probable neurite length on PCD was approximately 30 μm at day 5. The proportion of peaks ≧50 μm increased significantly on day 7.

The addition of equimolar amount of dopamine to diglycidyl 1,2-cyclohexanedicarboxylate in N,N-dimethylformamide (DMF) yielded PCD as a pale yellow powder that melted at 130-135° C. without noticeable degradation. Nuclear magnetic resonance (NMR) spectra revealed a change of chemical shift from approximately 3.2 ppm in the diglycidyl ester to 4.0 ppm in PCD, consistent with the opening of the epoxide ring. The intense C=O stretch at 1730 $cm^{-1}$ in Fourier-transformed infrared (FTIR) spectra confirmed the formation of the ester bonds, while the band at 866 and 814 $cm^{-1}$ revealed the presence of the catechol units in the polymer (FIG. 2). The absence of absorption at 1674 $cm^{-1}$, 1662 $cm^{-1}$, and 1564 $cm^{-1}$ indicated that oxidation of catechol to quinone was undetectable in PCD. For PCY, the presence of phenol was confirmed by a medium-intensity absorption at 834 $cm^{-1}$ (FIG. 2). Polymerization of dopamine converted its primary amine to a tertiary amine, which limited the formation of dopaminechrome, the oxidative intermediate to dopamine quinone. This increased the oxidative resistance of the catecholamine, thus minimizing the toxicity associated with dopamine quinone. The ester bond in PCD rendered the polymer biodegradable, with a half-life in phosphate buffered saline solution (PBS) of approximately 50 days at 37° C. (FIG. 3A). The ultimate degradation products, which are under investigation, are most likely to be N,N-bis(2,3-dihydroxypropyl)dopamine and 1,2-cyclohexane dicarboxylic acid.

Example 2

Biocompatibility of PCD

In vitro degradation, biocompatibility and nerve differentiation: PC D powders (10 mg) were compressed into 5 mm diameter, 0.5 mm thick pellets on a Carver press at 9000 lb for 2 min under $N_2$, and submerged into 15 ml sterile PBS solution in a centrifuge tube at 37° C. The disks were retrieved at pre-determined time point, dried in a vacuum oven at 50° C. and 100 mTorr overnight, and weighed.

PCD solution was filtered through a 0.2 μm filter and added to a 24 well-plate (100 μl/well), dried under vacuum for 3 days and washed with PBS. The plates were soaked in serum-free RPMI medium overnight. PCY, PDL, and laminin-coated plates subjected to the same washing and soaking treatment were used as controls.

PC12 cells were cultured in 85% RPMI 1640, 10% heat-inactivated horse serum (HHS) and 5% fetal bovine serum (FBS), and maintained in a humid, 5% $CO_2$ incubator at 37° C. PC12 cells were primed for 24 h in differentiation medium (RPMI 1640, 1% HHS and 0.5% FBS, 50 ng/ml NGF, and 20 μg/ml gentamycin) prior to seeding at a density of $1 \times 10^4/cm^2$. The cells were maintained in an incubator with medium exchanged every 2 days.

Cell morphology, neurite length measurements, and MTT assay: Cell morphology was monitored using an inverted phase contrast microscope at 200×. Neurite length, defined as the distance from the tip of the neurite to the junction between the cell body and neurite base, was measured on day 1, 3, 5, and 7. In the case of branched neurites, the length of the longest branch was used. For each well, 5-6 images were randomly acquired to ensure >500 cells were captured. Differentiation level was quantified by the percentage of differentiated cells with neurite longer than 20 μm. The average neurite length was calculated by dividing the total neurite length by the number of the cells with neurites. More than 500 cells was measured in each group at any given time point. The number of metabolically active cells was monitored by the MTT assay.

PCD's capability at promoting neurite outgrowth in vitro was evaluated using rat pheochromocytoma (PC 12) cells that have been widely used in studying neuronal communication and interaction between biomaterials and neurons. The cells were primed with NGF for 24 h instead of 9 days to better differentiate the materials' intrinsic ability of promoting neurite growth. To verify whether the catecholamine functional groups were recognized by the cells, a control material (PCY) based on tyrosine, the precursor of dopamine was synthesized. Cell proliferation, differentiation and morphology were also compared with PDL and laminin, the standard substrates for culturing many types of neurons.

The in vitro biocompatibility of PCD was evaluated by monitoring the number of adhered metabolically active cells using 3-(4,5-dimethylthiazol-2-yl)-2,5-diphenyltetrazolium bromide (MTT) assay as previously described. PCD appeared to be at least as biocompatible as standard neuron-culturing materials in vitro. The cell adhesion and proliferation on PCD resembled those of PDL (FIG. 3B). Cells reached confluence and started to detach from the surfaces after 7 days. PC12 cells with neurites longer than 20 μm are generally considered differentiated nerve cells. The differentiation level reached as high as 84±12% on PCD at day 5 (FIG. 3C). In comparison, the highest level of differentiation was 30±10%, 33±13% and 16±7.7% on PCY, PDL, and laminin respectively. PCD induced significantly more cell differentiation as culture time increased (ANOVA, P<0.05). In contrast, the percentage of differentiated cells on the controls remained in the 15-35% range and did not change significantly throughout the entire culture period.

The differentiated cells on all four materials exhibited neuron morphology. However, the median neurite length on PCD was significantly higher than that on the controls. Moreover, the difference between PCD and the control increased with time (FIG. 3D). At day 7, the neurites were approximately 150% longer than those on PCY, which yielded the longest neurites in the control group. The increase of median neurite length with time was significant on PCD, whereas the difference of neurite length on all control surfaces was statistically insignificant over the culture period.

The distribution of neurite length showed distinct patterns on PCD that were absent in the controls (FIGS. 3E, F). The neurite length was divided into 10 μm increment up to 100 μm and larger increments as appropriate above 100 μm. The percentage of neurite lengths within a defined range was plotted (for example, the data point at 50 μm represents the percentage of neurite length from 40 to 50 μm). Distinct peaks were visible on the PCD curves. As culture time increased, the fraction of longer neurites increased considerably, shifting the curve further to the right. The percentage of neurites more than 20-μm-long increased sharply at day 3, and reached as high as 77% on day 7. At day 5, approximately 20% of the neurites were longer than 50 μm, and the percentage nearly doubled at day 7. In contrast, less than 30% of the neurites were longer than 20 μm on the control materials throughout the culture period, and their neurite distribution curves showed fewer and less distinguishable peaks. A possible explanation for this difference is that differentiated PC12 cells developed distinct axons and dendrites on PCD, whereas the control materials did not induce neuronal differentiation sufficiently to reach such a stage.

The number of cells exhibiting typical neuron morphology was significantly higher on PCD than on the controls Neurites up to 180-μm-long began to appear on PCD 3 days after seeding, and grew up to 250 µm after 5 days of culture. In comparison, the longest neurites reached approximately 80 µm, 100 µm, and 60 µm on PCY, PDL, and laminin respectively. The nerve growth cone is a highly motile structure at the tip of an extending axon that explores the extracellular environment and guides the extension of the axon. The primary morphological characteristic of a growth cone in vitro is a sheet-like lamellipodium with numerous fine processes called filopodia. The cells on PCD displayed structures resembling growth cones at the end of their neurites. Growth cone-like structures were also observed on control surfaces. A number of cells on PCD exhibited extensive filopodia along their neurites in a similar fashion to the spines on spiny neurons. In contrast, the filopodia density was lower for the neurites on PCY. Low dopamine level has been shown to cause a reduction of dendritic spine density in dopaminoceptive neurons. The higher filopodia density on PCD indicated that the catecholamine functional groups could induce unique responses in differentiated PC12 cells.

Example 3

In Vivo Biocompatibility of PCD

In vivo biocompatibility: PCD pellets (20 mg, 5 mm diameter, 1 mm thick) were sterilized by plasma for 40 min. The implants were soaked in sterile PBS containing 0.1 w/v % ascorbic acid on an orbital shaker for 2 h prior to implantation. Male Sprague Dawley rats weighing 300-350 g were implanted with PCD under anesthesia maintained by halothane inhalation. Under sterile conditions, a gluteal muscle splitting technique was used to expose both sciatic nerves. Eight animals received two sterile implants with one implant placed directly underneath each sciatic nerve on the underlying muscle bed. Control animals (n=4) underwent either sham surgery, with exposure of both sciatic nerves followed by closure (n=3), or no surgery (n=1). The muscle layer was closed with vicryl sutures and the skin was closed with staples. Animals were cared for in compliance with protocols approved by the Committee on Animal Care of the Georgia Institute of Technology following NIH guidelines for the care and use of laboratory animals (NIH publication No. 85-23 rev. 1985).

Explants were harvested at 7, 14, 28, 60 days post-implantation. The surgical wounds were re-opened; the gluteal musculature was removed en bloc with the sciatic nerve and the polymer remnant, and fixed in 10% formalin for 3 days prior to histological analysis. The control tissues were similarly harvested and fixed at the same time points. The tissues were serially dehydrated in a graded series of ethanol and xylenes washes and embedded in paraffin. Ten micron thick sections were cut along the longitudinal axis of each implant. Sections were stained using a standard protocol for haematoxylin and eosin (H&E), and Mason's trichrome stain (MTS). The histological samples were analyzed blindly and independently by a histopathologist. Sections were analyzed for degree of inflammation and fibrosis. The inflammatory response to each implant was assessed by rating the levels of lymphocytic and histiocytic infiltrate; and fibrosis was identified by collagen deposition.

Preliminary in vivo biocompatibility studies indicated that PCD did not cause nerve degeneration or fibrous encapsulation when implanted immediately adjacent to rat sciatic nerves. The brown remnants of the 20 mg-implants were well-circumscribed with a cavitated center containing inflammatory infiltrates including phagocytic cells up to 8 weeks postimplantation. The absence of fibrosis would yield a more permissive environment for regenerating axons, and multi-month degradation time of the material would be beneficial for nerve regeneration, which usually requires several months.

Example 4

Characterization of PCA

Figure 4:
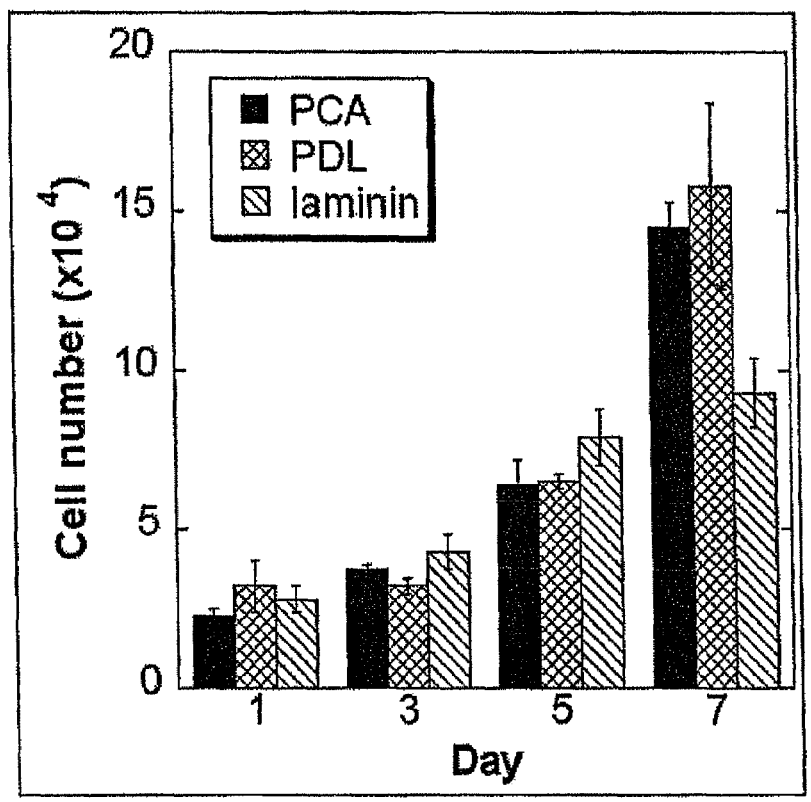
FIG. 4 is a bar graph showing that NGF-primed PC12 cell growth rate on PCA resembled that of the controls.

Two polymers containing acetylcholine functional groups were synthesized using 2-aminoethyl acetate with diglycidyl sebacate (see Scheme 1, resultant polymer abbreviated as PSA) and 1,2-cyclohexyldiglycidyl ester (resultant polymer abbreviated as PCA). PCA displayed a neuroinductive effect on differentiated PC 12 cells and primary rat DRG neurons. The cell growth rate matched that of PDL (FIG. 4). Long neurites up to 100 µm appeared at day 1. The neurite length and cell differentiation rate resembled that of PCD.

Example 5

Arginine Containing Polymer Synthesis and Characterization

Succinic acid was purchased from TCI. Arginine ethyl ester dihydrochloride was purchased from Research Organics. 1,3 meta chloro peroxy benzoic acid was purchased from Acros. All other chemical were purchased from Alfa Aesar and used without purification. Flash chromatography was done on a Buchi Fraction Collector C-660 w/UV photometer C-635. Nuclear magnetic resonance (NMR) spectra were recorded on a 400 MHz Mercury-400BB NMR. FTIR spectra were recorded on a ThermoNicolet IR-100 spectrometer. Dynamic light scattering measurements were recorded on a Zeta Potential/Particle Sizer NICOMP 380 ZLS. Aqueous phase gel permeation chromatography was performed on a Waters 2690 Separation Module with the 2410 UV/Vis and 2487 RI units using a 60 Å YMC-Pack Aqueous GPC column. The molecular weight and polydispersity of the polymer are reported relative to polyethylene glycol standards.

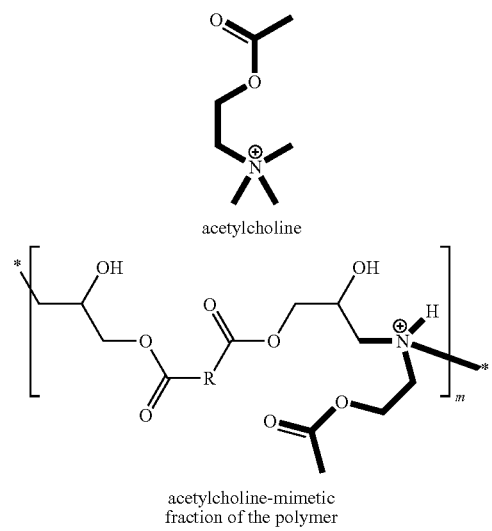

acetylcholine acetylcholine-mimetic fraction of the polymer

Monomer synthesis included preparing diallyl succinate by adding 8:1 molar amounts of allyl alcohol and succinic acid respectively, then adding concentrated sulfuric acid (0.1% volume of allyl alcohol) drop-wise to the solution. The reaction mixture was stirred and refluxed at 105° C. overnight. Sodium bicarbonate was added to the reaction to neutralize the sulfuric acid and the reaction mixture was rotovaped at 60° C. for 30 min followed by ethyl acetate/water extractions. Water in the organic phase was then removed by brine and anhydrous sodium sulfate overnight. The product can be stored at room temperature. $^1$H NMR (CDCl$_3$-d$_1$): 5.87 (m, 2H), 5.23 (m, 4H), 4.57 (d, 4H), 2.65 (s, 4H).

Diglycidyl succinate synthesis included 3:1 molar amounts of 1,3 meta chloro peroxy benzoic acid (mCPBA) and diallyl succinate respectively dissolved in dichloromethane (DCM). The reaction was stirred and refluxed at 40° C. for 5-6 h. Reaction mixture was then run through an ionic resin column containing tertiary amine beads. The product was further purified using low pressure liquid chromatography and the final product was stored under N$_2$ at –20° C. $^1$H NMR (CDCl$_3$-d$_1$): 4.40 (dd, 2H), 3.95 (q, 2H), 3.20 (m, 2H), 2.84 (t, 2H), 2.68 (s, 4H), 2.63 (q, 2H).

The arginine-based polymer was synthesized via polycondensation reaction of diglycidyl succinate and arginine ethyl ester, with 0.1% molar amount of Mg(ClO$_4$)$_2$ in anhydrous N,N-dimethylforamide (DMF) under N$_2$. The reaction mixture was stirred and kept at 60° C. for 7 days. The resultant polymer (PSR, Scheme 3) was placed under vacuum and heated to 60° C. for 24 h. PSR was then redissolved in methanol, washed with ethyl acetate, and placed under vacuum and heated at 60° C. overnight. The polymer was characterized by FTNMR, FTIR, differential scanning calorimetry, and gel permeation chromatography.

The polycondensation reaction between arginine ethyl ester and diglycidyl succinate yielded a pale yellow powder that is soluble in water, low molecular weight alcohols, and DMF. NMR spectra revealed the change in chemical shift from ~3.2 ppm in the diglycidol ester to ~4.0 ppm in PSR. This shift corresponds to the ring opening of the diglycidol ester. The intense C=O stretch at 1735 cm$^{-1}$ in the FTIR spectra confirmed the formation of ester bonds, and the intense band at 1673 cm$^{-1}$ with a shoulder at 1635 cm$^{-1}$ established the presence of the guanidine side chain associated with arginine. PSR has a melt temperature of 88.1° C. and a glass transition temperature of 42.8° C. according to differential scanning calorimetry measurements. The thermal properties of PSR indicate it will maintain its physical properties when exposed to the internal temperature of the body.

Example 6

Agarose Gel Retardation Assay

The 4.7 kb plasmid DNA, pEYFP-N1, contains the enhanced yellow fluorescent protein driven by the human CMV promoter. Plasmid DNA was amplified by insertion into JM-109 *E. coli*, and was purified using the Maxi-Prep DNA Purification kit from Qiagen. The purity of the plasmid DNA was measured by UV/Vis (TECAN Safire) with A$_{260}$/A$_{280}$ in the range of 1.7-1.85.

DNA/Polymer complexes were formed by adding 50 μL of plasmid DNA solution (0.04 μg/μL) in molecular grade water to 50 μL of polymer solution in molecular grade water. Polymer concentrations were altered to yield the desired N/P ratios. These mixtures were gently vortexed and allowed to incubate at room temperature for 45 minutes. From these mixtures, 10 μL was loaded on a 0.6% agarose gel with a 10% Ficoll 400 loading buffer (without bromophenol blue) in a 20 mM HEPES buffer. The gel was run at 108 V for 60 minutes and visualized by ethidium bromide staining.

The ability of a polymer to compact DNA through electrostatic interactions between the positively charged nitrogens of the polymer and the negatively charged phosphates in the DNA backbone is critical to its success in gene delivery. The ability of PSR to self-assemble with plasmid DNA was exhibited through an agarose gel retardation assay, particle size analysis, and zeta potential measurements.

Agarose gel electrophoresis separates molecules based on charge and size. Complete retardation of the DNA/polymer complex is a result of charge neutralization, and is one way to measure a polymer's aptitude to complex DNA. Polymer and DNA were both placed in solutions of molecular grade water, with the concentration of polymer changing to the desired N/P ratios. Polyplexes were formed by adding the DNA solution drop-wise to the polymer solution and then gently vortexing for 15 min. The resulting polyplex solution was then run on an agarose gel by gel electrophoresis. DNA was completely retarded at a N/P ratio between 4/1-8/1. From these results a N/P ratio of 10/1 was used for all further experiments to ensure the plasmid was completely compacted.

Agarose gel retardation assays can be beneficial by establishing the optimal polymer concentration to completely complex DNA, but it can not determine the actual size of the polyplexes formed nor the actual charge (zeta potential) carried by these polyplexes. Particle size and zeta-potential can be ascertained through dynamic light scattering (DLS) measurements. These measurements resulted in polyplexes that averaged 68 nm in diameter and carried a charge of +41 mV. Particles under 200 nm in diameter are capable of entering cells through the endocytotic pathway, so PSR/DNA complexes should not experience difficulty entering the cell. Also, the positive charge on the particles could improve interactions with negatively charged proteoglycans present on the cell surface.

Example 7

Particle Sizing and ζ-Potential Measurements

DNA/Polymer complexes were formed in the same manner as explained in the agarose gel retardation assay. Samples were diluted with 900 μL of molecular grade water and average particle sizes and ζ-potential measurements were carried out at 25° C. Three measurements were made on each sample, and the average diameter and ζ-potential were reported. The 10:1 PSR:DNA zeta potential was +41 mV. 3.5:1 PSR:DNA zeta potential was +20 mV. The size of particles formed at 3.5:1:PSR:DNA was approximately 70 and 130 nm, typically about 100 nm.

Example 8

Cytotoxicity Assay

Baboon smooth muscle cells (bSMCs) were cultured in 24-well tissue culture treated polystyrene plates at a seeding density of approximately 40,000 cells well in 1 ml of MCDB 131 growth medium (10% FBS/1% glutamine). Cells were grown overnight up to 70% confluency then growth medium was replaced with appropriate amounts of polymer and diluted with serum free medium to a total volume of 1 mL. This polymer media was filtered with a 0.2 μm before being used. Cells were incubated at 37° C., 5% CO$_2$ for 4 h, and then metabolic activity was measured by MTT assay. Polymer medium was replaced with 400 μl growth medium and 100 μl MTT solution (5 mg/mL), and incubated at 37° C. for 4 h. MTT media was removed, and replaced with 500 μl of lysis buffer (10% w/v sodium dodecyl sulfate in 0.01M HCl) following a D-PBS wash. Cells digest was incubated at room temperature for 1-2 h and absorbance of each sample was measured on a microplate reader (TECAN SAFIRE) at 560 nm.

Figure 5:
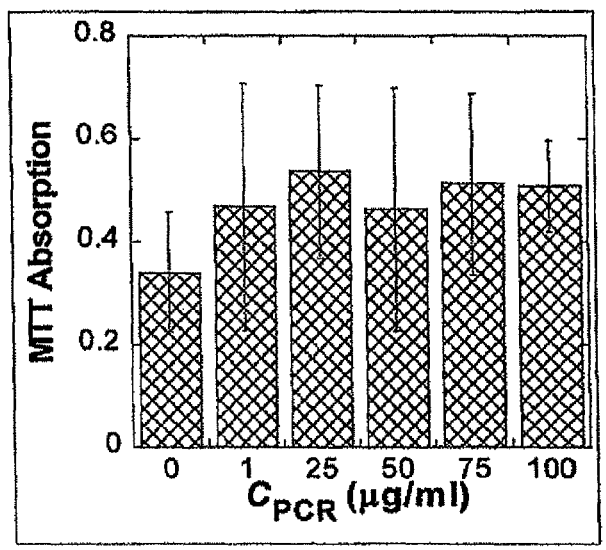
FIG. 5 is a bar graph showing that a biomaterial formed from arginine and 1,2-cyclohexyldiglycidyl (PCR) was safe to L2 cells at all concentrations tested.
Figure 6:
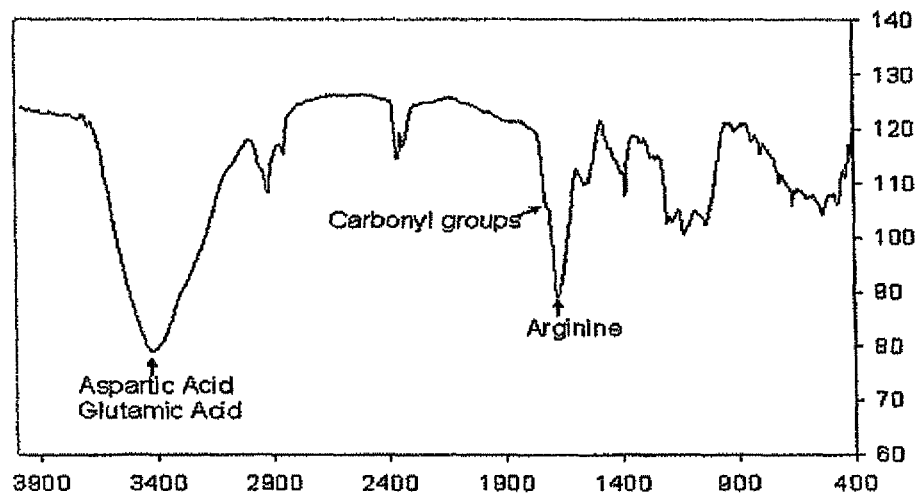
FIG. 6 shows an FTIR spectrum of PT-GREDV$_{100}$ confirming the presence of specific functional groups in the polymer.

PEI and PLL have both been used extensively in gene delivery and are considered two of the more well-known non-viral vectors. These vectors are often used as a basis of comparison for new cationic polymers in the field of gene therapy. PEI is considered successful due to its high transfection efficiency, and PLL was one of the first cationic vectors used and possess a biodegradable composition. Even with their advantageous qualities they both have limitations. The trade-off for PEI having a high transfection efficiency is its adeptness to be cytotoxic to cells. PLL has also been shown to be cytotoxic by inducing cell apoptosis in a wide variety of cell lines. MTT assay was used to measure the toxicity of PSR to bSMCs because this assay is a technique to measure cellular viability in the presence of a foreign substance.

bSMCs were incubated with various amounts of PSR for 4 hours, and then MTT assay was preformed to analyze the cytotoxic effects of our polymer (FIG. 5). Cells incubated with this polymer are 100% viable up to a concentration of 1 mg/ml. Compared to PEI (25 kD), which has shown to be cytotoxic to cells at a concentration as low as 20 µg/ml, PSR has demonstrated superior biocompatibility. Also, it has been shown poly-arginine peptides are cytotoxic to cells at a level of 5 µM. However, when arginine is incorporated into the backbone of our polymer it results in a biocompatible polymer. One possible reason for the discrepancy between the toxicities of polyarginine and PSR is that PSR degrades into a quadrol-like functional group which has been shown to promote wound healing. Other arginine-based vectors have also been reported having comparable level of biocompatibility. The cytotoxicity profile of PSR signifies its potential as a safe gene delivery vector.

Example 9

In Vitro Transfection

L2 cells were cultured in 24-well tissue culture treated polystyrene plates for at a seeding density of approximately 40,000 cells per well in 1 mL of Ham's F12k growth medium. Cells were grown overnight up to 70% confluency then growth medium was replaced with transfections medium. Polyplexes were prepared in the same manner as the agarose gel retardation assay, but prior to adding the plasmid DNA to the PSR solution it was complexed with a DNA intercalating agent, YOYO-1. The concentration of YOYO-1 used for 2 µg DNA was $4 \times 10^{-6}$ M and they were incubated at RT for 30 min before adding them to PSR solution. The polyplex solution was then diluted with serum free medium to a volume of 1 mL to form the transfection medium. Various N/P ratios were used with a constant amount of DNA, 2 µg, for each well. Linear PEI, 25 kD, was used as a positive control and was prepared in the same manner as the other polymer solutions. Other controls included naked plasmid DNA with and without YOYO-1, YOYO-1, and PSR/YOYO-1. Cells were incubated at 37° C., 5% $CO_2$ for 4-5 h and visualized by fluoresce using a Nikon Eclipse TE 2000-U microscope equipped with a FITC filter.

A gene delivery agent may be able to condense genetic information on a nanoscale, but it will be not be viewed as a successful delivery vehicle unless it can also transport this genetic material across the cell membrane. There are different techniques employed to measure a vector's ability to transport material into cells, and these methods can either be qualitative or quantitative. Some examples of these techniques include transfecting with a reporter plasmid (luciferace, eGFP) or fluorescently labeling the nucleic acid. The fluorescent dye YOYO-1 was used to track the movement of plasmid DNA in this series of transfections.

Plasmid DNA was intercalated with YOYO-1. This was then complexed with PSR to examine its capacity to deliver nucleic acids across the cell membrane. The polyplexes were observed inside of the cells 4-5 hours after transfection, similar to the positive control, linear PEI (25 kD) at a N/P ratio of 7/1. The polyplexes appeared to be contained within endosomes, as indicated by the punctated fluorescent signals. These data demonstrated that PSR can transport genetic information into cells.

PCR at unoptimized concentration exhibited higher transfection efficiency than PEI at optimized concentration reported in the literature in lung epithelial cells, L2, and prostate cancer cells, LNCaP. PEI is one of the most efficient nonviral vectors and is a standard to which new vectors are often compared. Further, PCR exhibited no cytotoxicity even at 100 µg/ml, whereas <30% of the cells were viable in the presence of 25 µg/ml PEI.

Other than arginine, side-chain protected lysine can be polymerized using the same method. After deprotection, the resultant polymer with cationic side chains will also serve as synthetic vectors for nucleic acid delivery. Oligomers of arginine or lysine and co-oligomers of the two cationic amino acids can be polymerized using the same method with potentially greater transfection efficiency.

Example 10

PSR and Heparin Sulfate Matrices

PSR (8 mg/ml), heparin sulfate (HS) (10 mg/ml), and bFGF (2 ug/ml) were prepared in solutions of D-PBS. The amount of PSR used relative to HS was a 35/1 molar ratio. Each sample contained 4 mg PSR, 114 µg, and 10 ng of bFGF. The bFGF solution was added to the PSR solution then the HS solution was added to the prior mixture. The order of addition can be changed. The resultant mixture was agitated and allowed to incubate at room temperature for ≧10 min. The mixture was then centrifuged, supernatant was removed, and 200 µl of D-PBS was added to resuspend the pellet. The pellets are ready for release study in PBS. For release in the presence of an enzyme, heparinase I (0.01 IU) (IBEX Pharmaceuticals) was added to each sample, and these were allowed to incubate at 37° C. for 48 h with agitation. Amount of bFGF present after the enzyme digest was quantified using a bFGF ELISA kit (R&D Systems).

Figure 9:
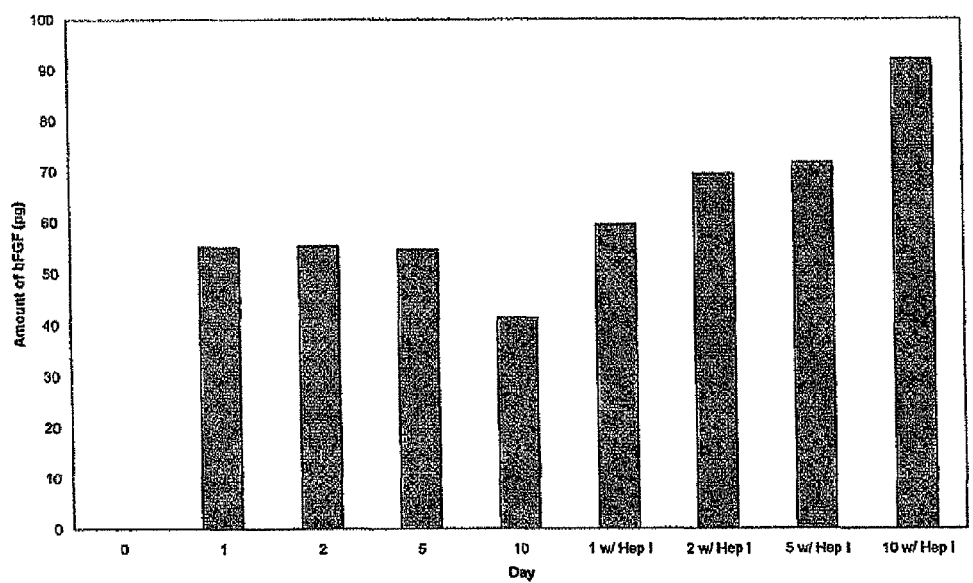
FIG. 9 are bar graphs showing the release profile of bFGF from PSR/HS networks. The amount of bFGF in the supernatant released from PSR/HS networks was measured over a period of time (t=1, 2, 5, and 10 days). This was done with or without the presence of Heparinase I and measured via ELISA analysis.

For the release profile of bFGF over time, samples were prepared in the same manner mentioned above (FIG. 9). After the resultant mixture was formed samples were incubated at 37° C. for a specified amount of time: 1, 2, 5, 10, and 15 days. At the specified time samples were centrifuged and 300 µl of the supernatant was removed and stored at −80° C. The bFGF concentration in each supernatant was quantified using a bFGF ELISA kit. Supernatant was also incubated with 0.001 IU of Heparinase I at 37° C. for 48 h and then bFGF concentration was quantified using a bFGF ELISA kit. Controls included using PSR and HS without any bFGF present at days 1 and 10.

Example 11

Bioactivity of bFGEF Contained within PSR/HS Nano-Networks

Micro- to nano-matices were assembled in the same manner as in Example 10 above. After centrifugation 3 ml of bSMC media was added to each well. At the appropriate time (24 h & 3 days) media was removed, partitioned, and either stored in −80° C. or exposed to a Heparinase I digest as mentioned in the release kinetics experiments. bSMCs were seeded in 24-well tissue culture treated polystyrene plate at a density of approximately 5,000 cells/well over night with bSMC media. Smooth cells were then washed twice with D-PBS and cultured with bSMC media without growth factors, bSMC media with control bFGF, and bSMC media with bFGF released from matrix. After 24 h and 3 days the smooth muscle cells were detached via trypsinization and counted on a Coulter Counter. The biological activity of bFGF released from nano-matrices was determined by comparing the stimulatory effects observed in wells containing control bFGF.

Nano- to micro-networks were prepared with and without bFGF and the presence of the growth factor (at such a low amount relative to PSR & HS) did not alter the morphology of the network. The network was composed of majority of fiber-like domains along with a minority of globular-like domains. Fibers of the networks range from ~100 nm to 20 μm and globular domains range from 5-20 μm in diameter. The factors that affect the fiber diameter appeared to include polymer/heparin ratio and solution concentration.

Statistical Analysis. For each variable group tested there were four replicates for the experimental and control samples. Multicomparisons ANOVA, Tukey Method, was used to statistically compare the different experimental values; $P<0.05$ was considered statistically significant. The results are reported as mean values with standard deviations.

What is claimed is:

1. A polymer comprising repeating units according to the following formula:

$$\left[ R_2\text{-}O\text{-}\underset{O}{\overset{O}{C}}\text{-}R_1\text{-}\underset{O}{\overset{O}{C}}\text{-}O\text{-}R_2\text{-}R_3 \right]_n$$

wherein $R_1$ is any alkyl, cycloalkyl, heterocycloalkyl, aryl, heteroaryl, or heterocycle wherein $R_1$ is optionally substituted with one or more functional group(s) selected from the group consisting of halide, alcohol, ether, thioether, tertiary amine, ketone, ester, and amide;

$R_2$ is any alkyl, cycloalkyl, aryl, or heteroaryl, wherein $R_2$ is optionally substituted with one or more functional group(s) selected from the group consisting of halide, alcohol, ether, thioether, tertiary amine, ketone, ester, and amide;

$R_3$ is a biomolecule selected from the group consisting of dopamine, glutamate, aspartate, histamine, norepinephrine, serotonin, taurine, glycine, 4-aminobutyrate, and methionine enkephalin, wherein $R_3$ is bound to $R_2$ via an amine bond; and n is >1.

2. The polymer of claim 1 that is produced from diglycidyl ester which is produced from a dicarboxylic acid.

3. The polymer of claim 2 wherein the dicarboxylic acid is selected from the group consisting of adipic acid, aldaric acid, aspartic acid, azelaic acid, camphoric acid, dimercaptosuccinic acid, fumaric acid, glutamic acid, glutaric acid, isophthalic acid, itaconic acid, ketoglutaric acid, maleic acid, malic acid, malonic acid, mesoxalic acid, n-acetylglutamic acid, oxalic acid, oxaloacetic acid, phthalic acid, phthalic acids, pimelic acid, sebacic acid, suberic acid, succinic acid, tartaric acid, terephthalic acid, traumatic acid, dodecanedioic acid, chaetomellic acids, ceriporic acids, 1, 2-cyclohexane dicarboxylic acid, and 1,4-cyclohexane dicarboxylic acid.

4. The polymer of claim 1, wherein the polymer is biodegradable.

5. The polymer of claim 1, further comprising an amino spacer.

6. The polymer of claim 1, wherein the polymer promotes axon growth relative to a control.

7. A polymer, produced by condensing monomers of dopamine with a diglycidyl ester, having the formula:

$$\left[ \underset{OH}{R_1}\text{-}O\text{-}\underset{O}{\overset{O}{C}}\text{-}R_3\text{-}\underset{O}{\overset{O}{C}}\text{-}O\text{-}\underset{OH}{R_2}\text{-}N\text{-}\text{CH}_2\text{CH}_2\text{-}\text{C}_6\text{H}_3(\text{OH})_2 \right]_n$$

wherein $R_1$ and $R_2$ are independently $C_1$-$C_{18}$; and $R_3$ is selected from the group consisting of alkyl, cycloalkyl, heterocycloalkyl, aryl, heteroaryl, and heterocycle; and wherein n is >1.

8. The polymer of claim 7, wherein the diglycidyl ester is 1,2 cyclohexyldiglycidyl ester.

9. A method for inducing neurite growth comprising contacting neural cells with the polymer of claim 7.

10. A method for inducing cell growth or regeneration comprising culturing one or more cells on the polymer of claim 1.

11. A method for delivering nucleic acid to a cell comprising packaging the nucleic acid in the polymer of claim 1 and contacting the cell with the packaged nucleic acid.

12. A method for inducing cellular differentiation comprising:

culturing one or more cells on the polymer of claim 1.

13. A method for delivering a nucleic acid to cell comprising combining the nucleic with the polymer of claim 1 and contacting a cell with the combination.

14. The polymer of claim 1 having the following structure

15. The polymer of claim 1, wherein n>1,000.

16. The polymer of claim 1, wherein n>10,000.

17. The polymer of claim 1, wherein n>100,000.

SEQUENCE LISTING

```
<160> NUMBER OF SEQ ID NOS: 4

<210> SEQ ID NO 1
<211> LENGTH: 5
<212> TYPE: PRT
<213> ORGANISM: artificial sequence
<220> FEATURE:
<223> OTHER INFORMATION: synthetic peptide sequence

<400> SEQUENCE: 1

Ile Lys Val Ala Val
1               5

<210> SEQ ID NO 2
<211> LENGTH: 5
<212> TYPE: PRT
<213> ORGANISM: artificial sequence
<220> FEATURE:
<223> OTHER INFORMATION: synthetic peptide sequence

<400> SEQUENCE: 2

Tyr Ile Gly Ser Arg
1               5

<210> SEQ ID NO 3
<211> LENGTH: 11
<212> TYPE: PRT
<213> ORGANISM: Human immunodeficiency virus

<400> SEQUENCE: 3

Tyr Gly Arg Lys Lys Arg Arg Gln Arg Arg Arg
1               5                   10

<210> SEQ ID NO 4
<211> LENGTH: 5
<212> TYPE: PRT
<213> ORGANISM: artificial sequence
<220> FEATURE:
<223> OTHER INFORMATION: synthetic peptide sequence

<400> SEQUENCE: 4

Gly Arg Glu Asp Val
1               5
```